US012564639B2

United States Patent
Bajpayee et al.

(10) Patent No.: US 12,564,639 B2
(45) Date of Patent: Mar. 3, 2026

(54) CATIONIC NANOSTRUCTURES FOR INTRA-CARTILAGE DELIVERY OF CONTRAST AGENTS AND DIAGNOSTIC USES THEREOF

(71) Applicant: Northeastern University, Boston, MA (US)

(72) Inventors: Ambika Bajpayee, Cambridge, MA (US); Chenzhen Zhang, Boston, MA (US); Armin Vedadghavami, Boston, MA (US); Tengfei He, Malden, MA (US)

(73) Assignee: Northeastern University, Boston, MA (US)

(*) Notice: Subject to any disclaimer, the term of this patent is extended or adjusted under 35 U.S.C. 154(b) by 0 days.

(21) Appl. No.: 18/310,234

(22) Filed: May 1, 2023

(65) Prior Publication Data

US 2024/0000953 A1 Jan. 4, 2024

Related U.S. Application Data

(62) Division of application No. 17/093,186, filed on Nov. 9, 2020, now abandoned.

(Continued)

(51) Int. Cl.

*A61K 9/00* (2006.01)
*A61K 31/573* (2006.01)

(Continued)

(52) U.S. Cl.

CPC ............ *A61K 47/60* (2017.08); *A61K 9/0019* (2013.01); *A61K 31/573* (2013.01); *A61K 38/18* (2013.01);

(Continued)

(58) Field of Classification Search

CPC ........................................................ A61K 47/60

See application file for complete search history.

(56) References Cited

U.S. PATENT DOCUMENTS 5,614,214 A 3/1997 Ahl et al.
9,289,506 B2 3/2016 Bajpayee et al.

(Continued)

FOREIGN PATENT DOCUMENTS

WO WO-2016/201323 A1 12/2016
WO WO-2017/173034 A1 10/2017

(Continued)

OTHER PUBLICATIONS

Vedadghavami, Cartilage penetrating cationic peptide carriers for applications in drug delivery to avascular negatively charged tissues, Acta Biomaterialia 93 (2019) 258-269 (Year: 2019).*

(Continued)

*Primary Examiner* — Paul W Dickinson

(74) *Attorney, Agent, or Firm* — Foley Hoag LLP; Dana M. Gordon; Laura A. Wzorek

(57) ABSTRACT

The present invention provides a platform for the delivery of small molecule drugs or contrast agents to joints and other soft tissues. The platform enables penetration of the drug through the full thickness of cartilage and long intra-cartilage residence time by leveraging electrostatic interactions between the cationic platform and the anionic cartilage matrix. Described herein are compounds and complexes that fit this platform. Also provided are methods of treating a joint disease with the compounds and complexes of the invention, and methods of imaging joints and other soft tissue.

13 Claims, 13 Drawing Sheets

Specification includes a Sequence Listing.

Related U.S. Application Data

(60) Provisional application No. 62/932,232, filed on Nov. 7, 2019.

(51) Int. Cl.
*A61K 38/18* (2006.01)
*A61K 47/22* (2006.01)
*A61K 47/60* (2017.01)
*A61K 47/64* (2017.01)
*A61K 49/04* (2006.01)
*B82Y 5/00* (2011.01)

(52) U.S. Cl.
CPC ............ *A61K 47/22* (2013.01); *A61K 47/645* (2017.08); *A61K 49/0438* (2013.01); *B82Y 5/00* (2013.01)

(56) References Cited

U.S. PATENT DOCUMENTS

| | | | |
|---|---|---|---|
| 10,226,427 | B2 | 3/2019 | Bajpayee et al. |
| 2014/0193508 | A1 | 7/2014 | Bajpayee et al. |
| 2021/0154307 | A1 | 5/2021 | Bajpayee et al. |
| 2021/0214217 | A1 | 7/2021 | Lodish et al. |

FOREIGN PATENT DOCUMENTS

| | | | |
|---|---|---|---|
| WO | WO-2018/106648 | A1 | 6/2018 |
| WO | WO-2020/191361 | A2 | 9/2020 |
| WO | WO-2020/191377 | A1 | 9/2020 |
| WO | WO-2024/039896 | A1 | 2/2024 |

OTHER PUBLICATIONS

Pouran, Multi-scale imaging techniques to investigate solute transport across articular cartilage, Journal of Biomechanics vol. 78, Sep. 10, 2018, pp. 10-20 (Year: 218).*

Jiang, Tumor Imaging by means of proteolytic activation of cell-penetrating pedptgides, PNAS,2004, 101(51), 17867-17892 (Year: 2004).*

Chang, Pentadecapeptide BPC 157 Enhances the Growth Hormone Receptor Expression in Tendon Fibroblasts, Molecules 2014, 19, 19066-19077, 2014). (Year: 2014).*

He et al., "Multi-arm Avidin nano-construct for intra-cartilage delivery of small molecule drugs," J. Control Release, 318: 33 pages (2020).

Kumar et al., "Biodegradable block copolymers", Advanced Drug Delivery Reviews, 53: 23-44 (2001).

Vedadghavami et al., "Cartilage penetrating cationic peptide carriers for applications in drug delivery to avascular negatively charged tissues," Acta Biomaterialia, 93: 258-269 (2019).

Warren et al., "Milk exosomes with enhanced mucus penetrability for oral delivery of siRNA", Biomaterials Science, 9(12): 4217-4512 (2021).

International Search Report and Written Opinion for International Application No. PCT/US2023/030686 dated Dec. 12, 2023.

* cited by examiner

1:4 mAv Intra-Cartilage Diffusion
Upstream
Downstream
$\tau_{Lag}$
$D_{EFF} \sim \frac{L^2}{\tau_{Lag}}$
1:4 mAv $C_D/C_U$, %
Time (min)

Healthy
50% GAG Depletion
Uptake Ratio ($R_U$)
Av
1:2 mAv
1:4 mAv

Av
1:2 mAv
1:4 mAv
1x PBS Desorption
10x PBS Desorption
% Retention inside cartilage
Time (days)

Healthy
50% GAG Depletion
SZ
DZ
200μm

1 Dexmethasone

2 Dex-SA
3 Dex-GA
4 Dex-PA

5 PEG-Dex-SA
6 PEG-Dex-GA
7 PEG-Dex-PA

SZ
Increasing GAG density
DZ

SZ
DZ
C
K'C
K'C
mAv-IOX
IOX
High negative FCD of cartilage

SZ
DZ
1 mm
0.5 mg I/mL IOX
0.5 mg I/mL mAv-IOX
HU
0
175
350
525
700

CATIONIC NANOSTRUCTURES FOR INTRA-CARTILAGE DELIVERY OF CONTRAST AGENTS AND DIAGNOSTIC USES THEREOF

RELATED APPLICATION

This application is a divisional of U.S. patent application Ser. No. 17/093,186, filed Nov. 9, 2020; which claims the benefit of priority to U.S. Provisional Patent Application No. 62/932,232, filed Nov. 7, 2019.

GOVERNMENT SUPPORT

This invention was made with government support under Grant No. R03EB025903 awarded by the National Institutes of Health, and Grant No. W81XWH-17-1-0085 awarded by the Department of Defense. The government has certain rights in the invention.

SEQUENCE LISTING

The instant application contains a Sequence Listing which has been submitted electronically in XML format and is hereby incorporated by reference in its entirety. Said XML copy, created on Apr. 24, 2023, is named NEX-06202_SL.xml and is 7,333 bytes in size.

BACKGROUND

Osteoarthritis (OA) is a common chronic inflammatory disease of the whole joint affecting knees, hips, fingers, and low spinal regions, and is one of the most disabling diseases in developed countries with an estimated social cost between 1 and 2.5% of gross domestic product. Traumatic joint injuries lead to development of post-traumatic OA (PTOA) within 10 years of injury in a majority of cases. Following a joint injury, there is an immediate increase in synovial fluid levels of inflammatory cytokines (e.g. interleukin-1 (IL-1), interleukin-6 (IL-6), and tumor necrosis factor alpha (TNF$\alpha$)) which diffuse into cartilage and rapidly initiate proteolysis and matrix loss. While several drugs have known potential to inhibit OA, none have yet translated to clinical practice as they suffer from poor cartilage targeting and off-target side effects.

Relatedly, early diagnosis of degenerative joint diseases like osteoarthritis (OA) is critical as there is only a narrow time-window during which therapeutic intervention can reverse disease progression. While computed tomography (CT) can diagnose changes in subchondral bone, it is not clinically viable for imaging joint soft tissues like cartilage that exhibit early degenerative changes associated with OA onset. CT may be developed for soft tissue imaging by using radio-opaque contrast agents injected into the joint, as long as they are safe and the time to produce sufficient CT attenuation is short enough to be clinically viable.

Currently, intra-articular (IA) injections to affected joints are the primary route for directly delivering pain and inflammation relievers, however, a majority of drug is rapidly cleared from the joint space, therefore requiring multiple injections of high drug doses which causes systemic toxicity. This problem is further aggravated by the complex architecture of avascular cartilage containing a dense meshwork of collagen, interspersed with a high density of negatively charged aggrecan-associated glycosaminoglycans (GAGs) which hinder drug penetration. Breakdown of articular cartilage triggers production of various inflammatory cytokines which disturb chondrocyte homeostasis, causing these cells to produce more matrix degrading agents than matrix generating agents. It is therefore critical for drugs to reach their cell and matrix targets sites, requiring novel strategies to enhance localization of OA drugs to target chondrocytes. Currently there are no delivery systems that can (i) locally and safely target cartilage and enable drugs to penetrate through the full depth of tissue to reach chondrocytes and matrix targets, (ii) bind within cartilage to prevent their diffusion back out to the synovial fluid, and (iii) provide sustained drug release over several days to weeks. None of the drug delivery systems proposed thus far (e.g. drug-encapsulating micelles, liposomes, polymeric particles, aggregating hydrogels, etc.) are able to penetrate the cartilage or bind with its cell/matrix targets.

Similarly, contrast agents like ioxaglate (IOX) are anionic and thus repelled by the negatively charged cartilage matrix containing a high density of GAGs. This hinders the intra-tissue penetration and partitioning of the contrast agents, and results in poor CT attenuation. These contrast agents are also rapidly cleared from the joint space, thus exhibiting short intra-tissue residence time. Higher doses of contrast agents are therefore required to enhance flux and achieve intra-cartilage concentrations sufficient for CT imaging. Such high dosages result in both local and systemic toxicity.

The high negative fixed charge density (FCD) of cartilage resulting from the high density of negatively charged GAG chains provides a unique opportunity to use electrostatic interactions for enhancing transport, uptake and retention of cationic drug carriers. Using short length cationic peptide carrier motifs, it was shown recently that there exists an optimal net positive charge to deliver a drug of given size to a tissue of known FCD that will result in rapid penetration through the full thickness of cartilage before a majority of it is cleared from the joint space, providing the highest intra-cartilage uptake and long-term retention [1]. Optimal net positive charge on the carrier is chosen to enable weak and reversible binding with the intra-tissue negatively charged groups such that the drug and its carrier can penetrate through the full tissue thickness and not get stuck in the tissue's superficial zones. Despite weak binding, the high negative FCD of aggrecan associated GAGs inside cartilage greatly increases the residence time of optimally charged cationic drug carriers. Similarly, the cationic glycoprotein, Avidin, due to its optimal net size (<10 nm hydrodynamic diameter) and charge (between +6 and +20) was shown to penetrate through full thickness of rabbit cartilage following IA injection [2], resulting in a high intra-cartilage uptake ratio of 180 (implying 180× higher concentration of Avidin inside cartilage than surrounding fluid at equilibration). Further, Avidin was found to be present through the full thickness of cartilage two weeks following its IA administration in a rabbit anterior cruciate ligament transection (ACLT) model of PTOA [3]. Avidin was covalently conjugated with 4 moles of Dexamethasone (Av-Dex) using its four biotin binding sites [4] and administered in a single low dose IA injection one week following ACLT in a rabbit model. Av-Dex suppressed injury induced joint inflammation, synovitis, incidence of osteophyte formation and restored trabecular properties at 3 weeks significantly greater than free Dex. However, to deliver even a single low dose of 0.5 mg Dex, a high dose of 20 mg Avidin was required due to the low drug loading content of the conjugate. This design results in enhanced GAG loss from cartilage. Moreover, a high dose of Avidin can reduce intra-tissue osmotic swelling pressures owing to its cationic charge leading to decreased water content and potential loss of proteoglycans. By contrast, Avidin doses less than 100 μM have been shown to not affect GAG loss, chondrocyte viability or biosynthesis rates of proteins and GAGs in bovine cartilage explants.

Therefore, there exists a need to develop a conjugate system with an increased drug loading content for delivering effective doses of drugs or contrast agents, which leverages the cartilage homing property of Avidin, while decreasing the overall dosage of Avidin, thus minimizing the GAG loss caused by Avidin.

SUMMARY OF INVENTION

In certain aspects, the present invention provides a compound, comprising:

a residue of biotin;

a multi-arm polymeric scaffold;

one or more hydrolyzable linking moieties; and one or more residues of an active pharmaceutical ingredient;

wherein the residue of biotin is covalently attached to the multi-arm polymeric scaffold;

each of the one or more hydrolyzable linking moieties are covalently attached to the multi-arm polymeric scaffold; and each of the one or more residues of the active pharmaceutical ingredient are covalently attached to each of the one or more hydrolyzable linking moieties.

In other aspects, the present invention provides a complex, comprising avidin and one or more compounds described herein.

The present invention also provides methods of treating a joint disease in a subject, the method comprising administering to the subject a compound or complex described herein.

The present invention also provides methods of preventing glycosaminoglycan (GAG) loss in a subject in need thereof, comprising administering to the subject a compound or complex described herein.

In further aspects, the present invention provides a compound comprising:

a residue of biotin;

a multi-arm polymeric scaffold; and one or more residues of a contrast agent;

wherein the residue of biotin is covalently attached to the multi-arm polymeric scaffold; and each of the one or more residues of a contrast agent are covalently attached to the multi-arm polymeric scaffold.

In other aspects, the present invention provides a complex, comprising avidin and one or more such compounds described herein.

Also provided herein is a method of diagnosing a joint disease, comprising administering to a subject a compound or complex described herein.

Also provides are methods of imaging soft tissue, comprising administering to a subject a compound or complex of the invention, and imaging the soft tissue.

Also provided herein are methods of delivering a contrast agent or an active pharmaceutical ingredient to a negatively charged tissue in a subject, comprising administering to the subject a complex;

wherein the complex comprises a residue of a contrast agent or an active pharmaceutical ingredient and a cationic peptide, wherein the peptide comprises from 2 to 40 amino acid residues, and the net charge of the peptide is from +7 to +20 inclusive; and the residue of the contrast agent or the active pharmaceutical ingredient is covalently bonded to the peptide.

BRIEF DESCRIPTION OF THE DRAWINGS

FIG. 4A shows a schematic of Dex conjugation with 8-arm PEG-amine using cross linkers (R: SA, GA and PA) to form ester linkers with varying carbon spacer lengths (X: $X_1$, $X_2$ and $X_3$).

FIG. 4B shows the corresponding Dex release rates at 37° C., pH 7.4 in PBS. Controlled release PEG-Dex (2:1:1) represents Dex conjugated using combination of ester linkers synthesized from SA, GA and PA in 2:1:1 molar ratio of Dex.

FIG. 4C shows a mechanism of fast hydrolysis of PEG-Dex-SA (5) in PBS (pH 7.4). Carbonyl in amide bond, an electron withdrawing group (EWG), withdraws electrons from methylene and ester bonds (inductive effect) thereby decreasing ester bond's electron density and making it more electrophilic ($\delta^+$) and reactive to nucleophilic attack from hydroxide ion ($^-OH$) causing faster hydrolysis of the ester bond. Repulsion between hydrophilic PEG and hydrophobic Dex further strains the ester linker making it unstable. When $X_1$ is replaced by $X_2$ or $X_3$, the carbon spacer length is increased that weakens the inductive effect of carbonyl and donates more electrons to stabilize the ester bond. This also reduces the repulsive effects between PEG and Dex.

FIG. 4D is a bar graph showing results of a cytotoxicity test: % cell viability in cartilage explants following 48 h treatment with PEG-Dex-SA, PEG-Dex-GA, and PEG-Dex-PA.

FIG. 6A shows nitrite released to the medium per mg cartilage tissue on Day 2 and Day 8.

FIG. 6B shows chondrocyte metabolism measured as relative fluorescence units (RFU) using alamarBlue assay on Day 16. (* vs untreated, #vs IL-1α, $ vs single dose Dex of same concentration, $p<0.05$. Statistical markers are color coordinated with the bars.)

DETAILED DESCRIPTION OF THE INVENTION

The present invention is based on the surprising discovery that a cationic multi-arm Avidin (mAv) nano-construct enables intra-cartilage delivery of small molecule drugs and imaging contrast agents. The construct enables delivery of the desired agent in high concentrations through the full thickness of the cartilage by leveraging electrostatic interactions between the high negative fixed charge density (FCD) of cartilage and the cationic nano-construct.

Electrostatic interactions enable high partitioning up of the nano-construct at the cartilage interface increasing its concentration from C to KC, where K is the Donnan partitioning factor (FIG. 8A-8B), which enhances its rate of penetration into cartilage.

Figures 8A, 8B, 8C:
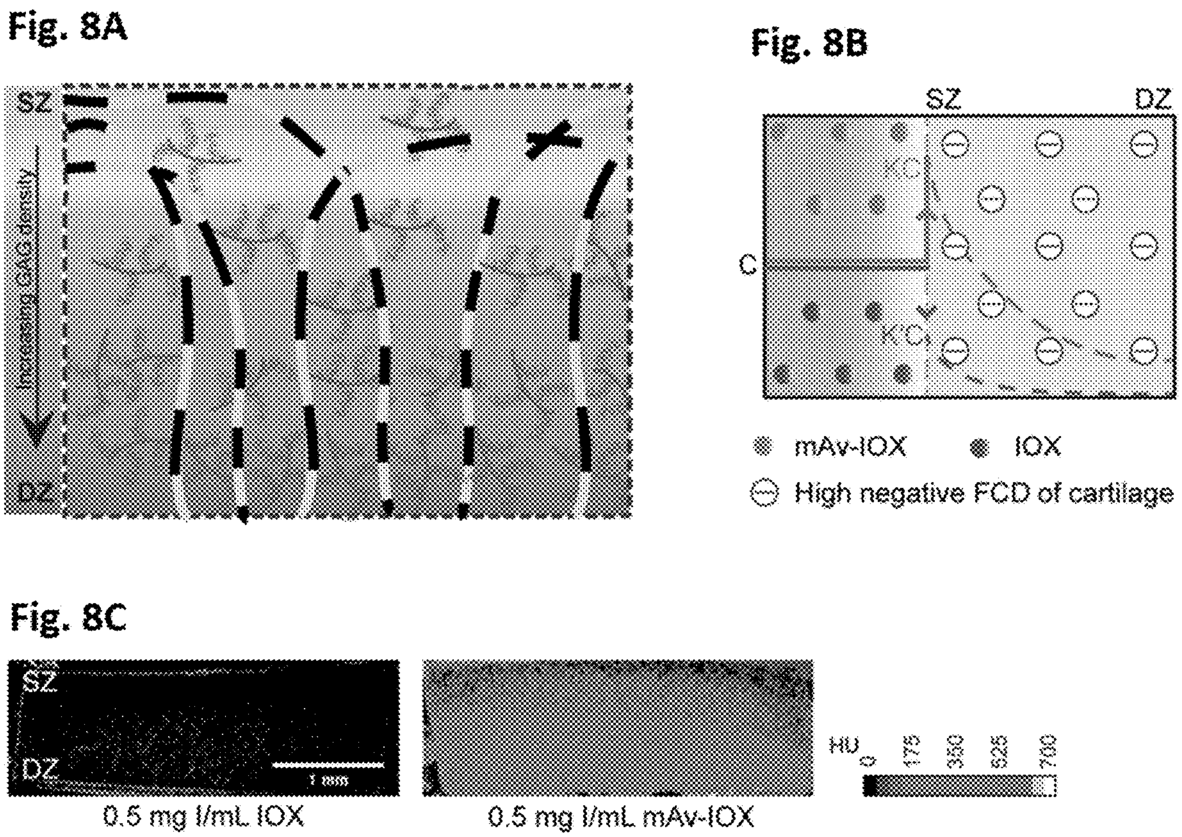
FIG. 8A depicts the structure of cartilage tissue showing increasing concentration of negatively charged GAGs from superficial zone (SZ) to deep zone (DZ) of tissue giving it a high negative fixed charge density (FCD).
FIG. 8B shows cationic contrast agent, mAv-IOX, due to its optimal net charge can rapidly penetrate through the full thickness of cartilage in high concentrations owing to high Donnan partitioning factor (K) that increases its concentration at tissue interface by KC. On the contrary, transport of anionic IOX is hindered by negatively charged cartilage whose concentration at cartilage interface partitions down by K'C.
FIG. 8C shows mAv-IOX results in high CT signal inside cartilage at a low concentration of 0.5 mg I/mL while anionic IOX cannot.

Typically, a contrast agent such as anionic IOX is repelled by the negatively charged cartilage matrix resulting in partitioning down by K'C reducing IOX's rate of transport and uptake into the tissue. By contrast, a contrast agent conjugated to the mAv nano-construct, with an enhanced rate of cartilage penetration, enables high CT attenuation even at low doses for safe diagnosis of early stage OA (FIG. 8C). The technology also has the potential for clinical CT of other negatively charged joint soft tissues.

Figure 1:
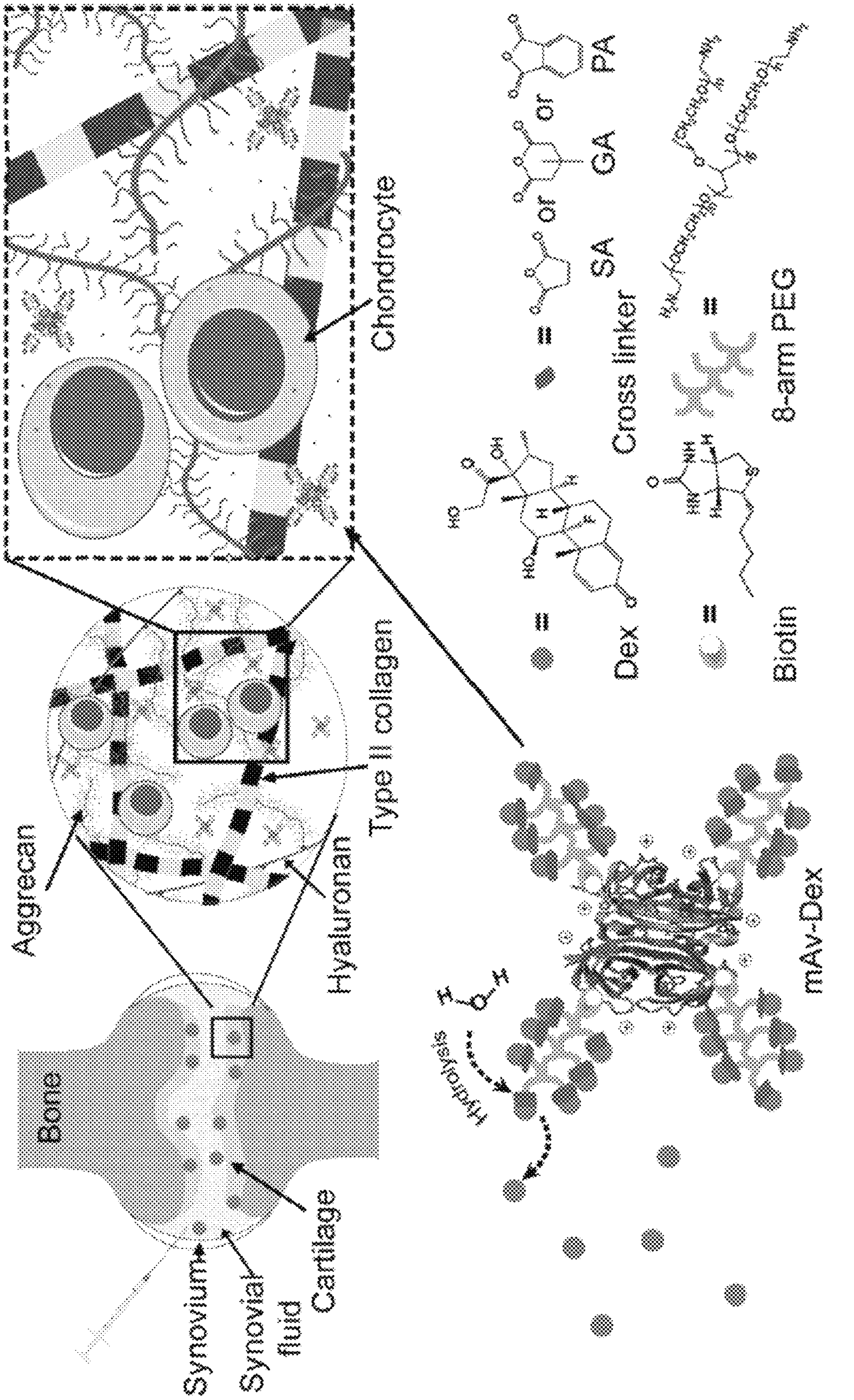
FIG. 1 depicts a schematic of charge-based intra-cartilage drug delivery of the nano-construct multi-arm Avidin conjugated with a small molecule drug, Dexamethasone (mAv-Dex) by using hydrolysable ester linkers derived from succinic, glutaric and phthalic anhydrides (SA, GA, PA) in 2:1:1 molar ratio enabling tunable (and long) drug release half-lives. Following its intra-articular administration, mAv-Dex can rapidly penetrate through the full thickness of negatively charged cartilage in high concentrations due to electrostatic interactions thereby creating an intra-cartilage drug depot. The optimal net positive charge of mAv enables its rapid and high intra-cartilage uptake and long-term retention via weak-reversible binding with negatively charged aggrecans. Therapeutic doses of drug (Dex) is then released via hydrolysis from mAv over several days, which can reach the chondrocytes to bind with its glucocorticoid receptors triggering downstream signaling pathways and suppressing OA associated catabolic activity. This intra-cartilage depot drug delivery platform can be used to deliver a variety of drugs or combination of drugs and enable OA treatment with only a one shot injection of low drug doses thereby eliminating toxicity issues associated with multiple injections of high drug doses that are currently needed to maintain sustained drug doses within the joint.

Moreover, the nano-constructs of the invention enable greater delivery of a therapeutic agent in a single low-dose of the construct, due to the many sites on the mAv construct that may be conjugated to the therapeutic agent. As shown herein, multi-arm Avidin contains 28 sites for covalent conjugation of drugs (FIG. 1) compared to 4 sites in previous designs [4]. Conjugation of dexamethasone (Dex) as an example small molecule drug to mAv (mAv-Dex) by using a combination of hydrolysable ester linkers derived from succinic anhydride (SA), 3,3-dimethylglutaric anhydride (GA) and phthalic anhydride (PA) enabled sustained controlled release of Dex in therapeutic doses over several days. Using in-vitro cytokine-challenged bovine cartilage models of OA, we show that a single low dose of mAv-Dex can effectively suppress cytokine-induced GAG loss, cell death and inflammatory response significantly better than free (unmodified) Dex over 2 weeks. With this multi-arm design, less than 1 μM Avidin was needed—a dose that did not cause any GAG loss or cytotoxicity. The release rate of the conjugated therapeutic agent can be modulated by using a combination of ester linkers with different rates of hydrolysis based on type of drug, its target sites and the state of the disease. This nano-construct thus has high translational potential for enabling intra-cartilage delivery of a broad array of small molecule OA drugs and their combinations to chondrocytes without the previously contemplated side effects.

Definitions

The term "residue" as used herein means a portion of a chemical structure that may be truncated or bonded to another chemical moiety through any of its substitutable atoms. As an example, the structure of dexamethasone is depicted below:

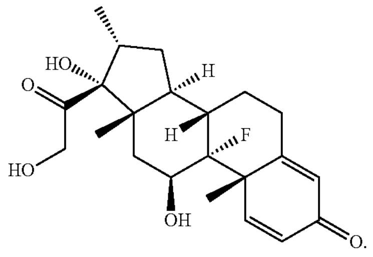

(dexamethasone)

Residues of dexamethasone include, but are not limited to, any of the following structures:

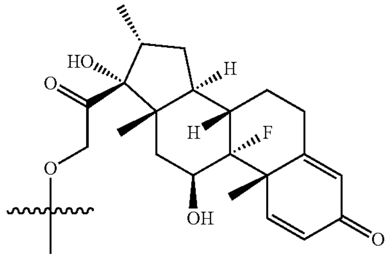

and

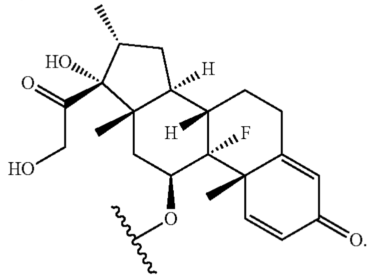

The term "hydrolyzable linking moiety" means a chemical group that undergoes a breaking of a chemical bond when reacted with water or a hydroxide ion under certain conditions, such as physiological conditions.

An "active pharmaceutical ingredient" is a substance having pharmacological activity or other effect in the treatment, cure, diagnosis, mitigation, or prevention of a disease. The term also encompasses substances having an effect in restoring, halting, correcting, or modifying physiological functions.

When used in a polymeric scaffold, multi-arm polyethylene glycol can consist of 2 repeat units of ethylene glycol up to 500,000 repeat units of ethylene glycol. In some embodiments, the number of repeat units of PEG is from 2 to 100,000, from 2 to 50,000, from 2 to 25,000, from 2 to 10,000, from 2 to 7500, from 2 to 5000, from 2 to 2500, from 2 to 1000, from 2 to 500, from 2 to 250, from 2 to 100, from 2 to 75, or from 2 to 50 repeat units. The average molecular weight of the PEG moiety may be about 1000 Da to about 100,000 Da, about 5000 Da to about 50,000 Da, about 1000 Da to about 50,000 Da, about 5000 Da to about 15,000 Da, or about 10,000 Da. The terminal groups of the multi-arm PEG used to manufacture the scaffolds of the invention may be modified with a functional group such as an amine. In preferred embodiments, the PEG used in the polymeric scaffold is 8-arm PEG, more preferably 8-arm PEG-$NH_2$.

A carbonyl group means —C(═O)—.

An amine group means —$NH_2$ or —NH(hydrocarbyl), or —N(hydrocarbyl)$_2$.

The term "hydrocarbyl", as used herein, refers to a group that is bonded through a carbon atom that does not have a ═O or ═S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a ═O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by the FDA Office of Biological Standards.

The complexes of the invention may optionally contain a pharmaceutically acceptable excipient.

As used herein, the term "pharmaceutically acceptable excipient" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable excipients include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

The present invention also contemplates pharmaceutically acceptable salts of the compounds of the invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Preferably the administration is intraarterial.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Embodiments of the Invention

The present invention provides a platform for the delivery of small molecule drugs or contrast agents to joints and other soft tissues. The platform enables penetration of the drug through the full thickness of cartilage and long intra-cartilage residence time by leveraging electrostatic interactions between the cationic platform and the anionic cartilage matrix. Embodiments of the invention are described below.

In certain embodiments, the present invention provides a compound, comprising:

a residue of biotin;

a multi-arm polymeric scaffold;

one or more hydrolyzable linking moieties; and one or more residues of an active pharmaceutical ingredient;

wherein the residue of biotin is covalently attached to the multi-arm polymeric scaffold;

each of the one or more hydrolyzable linking moieties are covalently attached to the multi-arm polymeric scaffold; and each of the one or more residues of the active pharmaceutical ingredient are covalently attached to each of the one or more hydrolyzable linking moieties.

In certain embodiments, the residue of biotin is covalently attached to the multi-arm polymeric scaffold on a different arm than the one or more hydrolyzable linking moieties.

In certain embodiments, the compound comprises two or more hydrolyzable linking moieties, wherein each hydrolyzable linking moiety is covalently attached to a different arm of the multi-arm polymeric scaffold.

In certain embodiments, one arm of the multi-arm polymeric scaffold is covalently attached to the residue of biotin, and each of the remaining arms of the multi-arm polymeric scaffold is attached to a hydrolyzable linking moiety, and each hydrolyzable linking moiety is attached to a residue of an active pharmaceutical ingredient.

In certain embodiments, the multi-arm polymeric scaffold comprises at least 3 arms. In certain embodiments, multi-arm polymeric scaffold comprises at least 4 arms or at least 6 arms. In certain embodiments, the multi-arm polymeric scaffold comprises 8 arms. In certain such embodiments, the compound comprises 8 hydrolyzable linking moieties and 8 residues of an active pharmaceutical ingredient.

In certain embodiments, the multi-arm polymeric scaffold comprises a hydrophilic polymer. Exemplary hydrophilic polymers useful in the compounds of the invention include polyacrylamide, polyurethanes, poly (hydroxyethyl methacrylamide), and polyethylene glycol. In certain embodiments, the multi-arm polymeric scaffold may be a multi-arm polyethylene glycol scaffold.

Multi-arm polymers encompass numerous configurations that are useful in the compounds, complexes, and methods of the invention. These configurations include star polymers, hyperbranched polymers, dendrimers, graft polymers, and polymer networks.

In certain embodiments, the polymeric scaffold comprises a star polymers. Star polymers include, but are not limited to, copolymers based on polyethylene oxide (PEO) and poly(methyl methacrylate) (PMMA); copolymers based on PMMA-PAA (poly(acrylic acid)); N-(2-hydroxypropyl) methacrylamide (HPMA) copolymers; poly(styrene) core and poly(tert-butyl acrylate) arms; thiol terminated multi-arm (6 and 8) poly(ethylene-glycol) (PEG); also PEG-PAMAM. In the complexes of the invention (e.g., in which avidin is the core), such polymers form core cross-linked star polymers.

In certain embodiments, the polymeric scaffold comprises a hyperbranched polymer. Hyperbranched polymers may include monomers such as polyester, polyesteramine, polyamine, polyester, polyglycerols, polyphosphate, polyglycerols-PEG.

In certain embodiments, the polymeric scaffold comprises a polypeptide system including polycationic conjugates poly [Lys (DL-Alam-Leui)] (ALK), poly [Lys(Ser-DL-Ala3)] (SAK) amphoteric poly[Lys(Glu-DL-Ala3)] (EAK). In further embodiments, the polymeric scaffold comprises a polymer such as Poly (beta-amino ester) (PBAE) or Chitosan.

In certain embodiments, each of the one of more hydrolyzable linking moieties comprises a carbonyl group. In further embodiments, each of the one of more hydrolyzable linking moieties is selected from the group consisting of

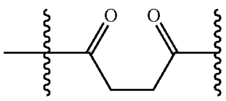
,
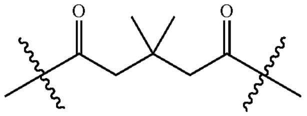
, and

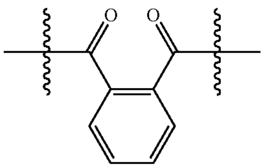
.

In certain embodiments, each of the one of more hydrolyzable linking moieties is

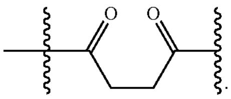 [SMILES: *C(=O)CCC(*)=O]
.

Alternatively, each of the one of more hydrolyzable linking moieties may be

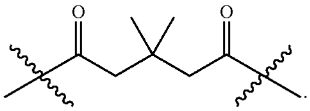 [SMILES: *C(=O)CC(C)(C)CC(*)=O]
.

Alternatively, each of the one of more hydrolyzable linking moieties is

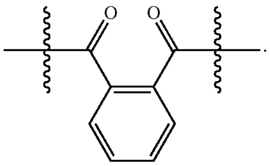 [SMILES: *C(=O)c1ccccc1C(*)=O]
.

In certain embodiments, the active pharmaceutical ingredient is a glucocorticoid or pharmaceutically acceptable salt thereof. Exemplary glucocorticoids include cortisol, cortisone, prednisone, prednisolone, methylprednisolone, dexamethasone, betamethasone, triamcinolone, fludrocortisone, deoxycorticosterone, aldosterone, and beclometasone. In certain embodiments, the glucocorticoid is dexamethasone, triamcinolone, or prednisone; preferably dexamethasone.

In further embodiments, the active pharmaceutical agent is a protein, such as insulin link growth factor-1 (IGF-1).

In certain embodiments, the multi-arm polymeric scaffold comprises an 8-arm polyethylene glycol scaffold;

each of the one of more hydrolyzable linking moieties is selected from the group consisting of

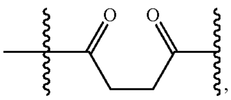
,

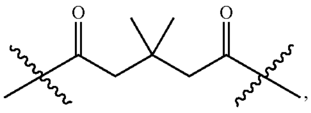
, and

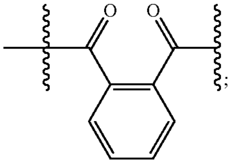
;

and the active pharmaceutical ingredient is dexamethasone.

In certain embodiments, the compound has the following structure:
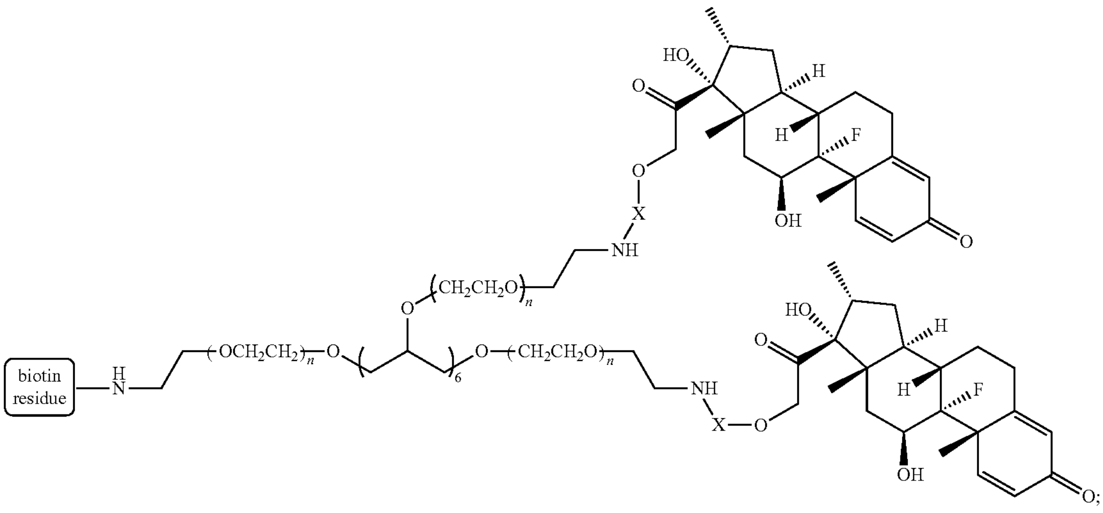
wherein X is a hydrolyzable linking moiety selected from the group consisting of
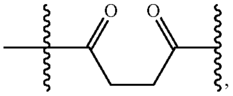
,
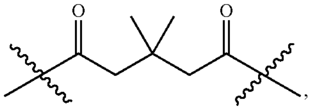
, and
-continued
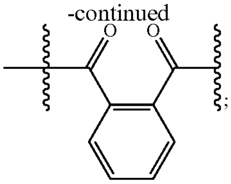
;
and
n is an integer from 1 to 500,000;
or a pharmaceutically acceptable salt thereof.
In further embodiments, the compound has the following structure:
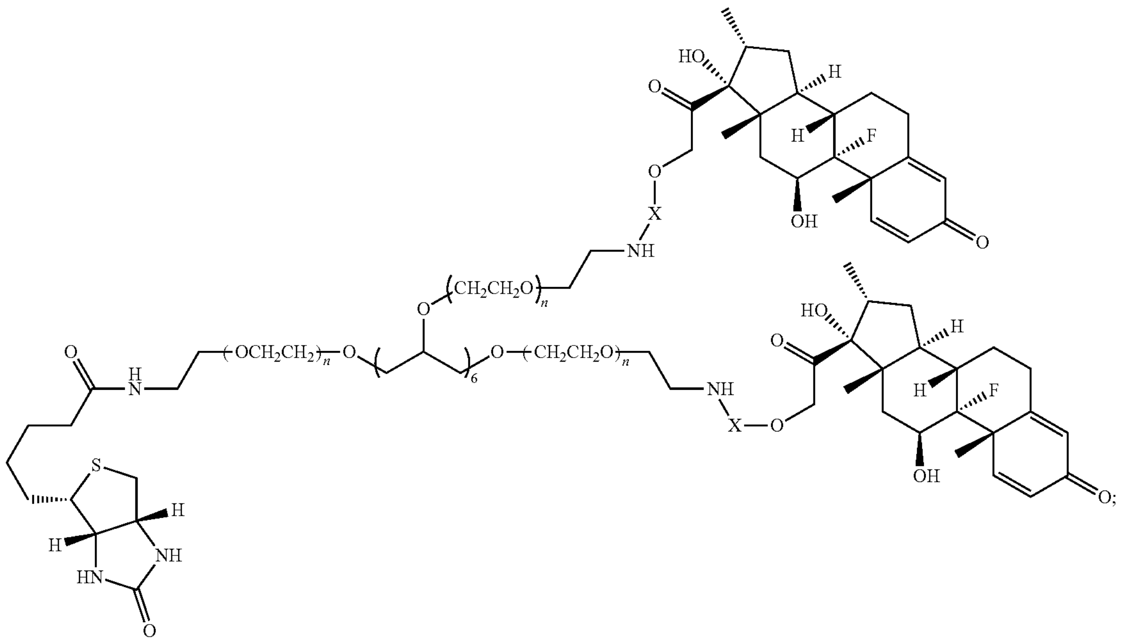
;

wherein X is a hydrolyzable linking moiety selected from the group consisting of

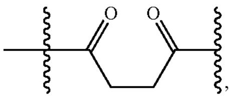 [SMILES: *C(=O)CCC(*)=O]

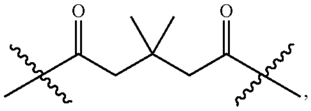

, and

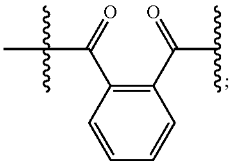

and n is an integer from 1 to 500,000;

or a pharmaceutically acceptable salt thereof.

In further aspects, the present invention provides a complex comprising avidin and one or more compounds described herein. In certain embodiments, the one or more compounds are bound to avidin through electrostatic interactions.

In certain embodiments, avidin and the one or more compounds are in a molar ratio of 1:4; and all four biotin-binding sites of avidin are bound to one of the one or more compounds.

In certain embodiments, the complex comprises four compounds described herein, wherein the four compounds are identical to each other.

In certain embodiments, the complex comprises four compounds described herein, wherein at least one compound is different from the other compounds.

In certain embodiments, the complex comprises four compounds described herein, wherein at least two compounds are different from each other and from the other compounds.

In certain embodiments, the complex comprises four compounds described herein, wherein all four compounds are different from each other.

In certain embodiments of the complex comprising four compounds of the invention, in all four compounds X is

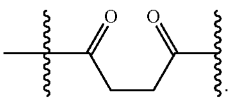

In certain embodiments of the complex comprising four compounds of the invention, in all four compounds X is

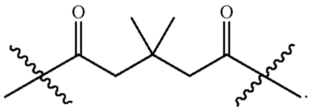 [SMILES: *C(=O)CC(C)(C)CC(*)=O]

In certain embodiments of the complex comprising four compounds of the invention, in all four compounds X is

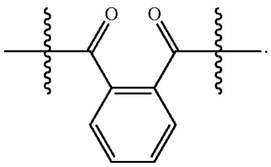 [SMILES: *C(=O)c1ccccc1C(*)=O]

In certain embodiments of the complex comprising four compounds of the invention, in two compounds X is

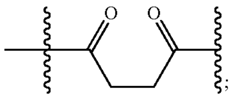 [SMILES: *C(=O)CCC(*)=O]

in one compound X is

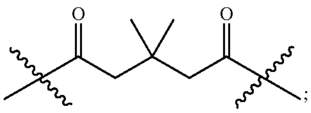 [SMILES: *C(=O)CC(C)(C)CC(*)=O]

and in one compound X is

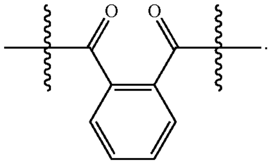 [SMILES: *C(=O)c1ccccc1C(*)=O]

The present invention also provides methods of treating a joint disease in a subject in need thereof, comprising administering to the subject a compound described herein or a complex described herein. In certain embodiments, the method comprises administering a complex described herein.

In certain embodiments, the joint disease is selected from the group consisting of rheumatoid arthritis, spondyloarthritis, juvenile idiopathic arthritis, lupus, gout, bursitis, and osteoarthritis. In certain embodiments, the joint disease is osteoarthritis.

In certain embodiments, administering a compound or complex described herein comprises intra-articular injection.

The present invention also provides methods of preventing glycosaminoglycan (GAG) loss in a subject in need thereof, comprising administering to the subject a compound described herein or a complex described herein. In certain embodiments, the method comprises administering a complex described herein.

The present invention also provides compounds, comprising:

a residue of biotin;

a multi-arm polymeric scaffold; and one or more residues of a contrast agent;

wherein the residue of biotin is covalently attached to the multi-arm polymeric scaffold; and each of the one or more residues of a contrast agent are covalently attached to the multi-arm polymeric scaffold.

In certain embodiments, the residue of biotin is covalently attached to the multi-arm polymeric scaffold on a different arm than the one or more residues of a contrast agent.

In certain embodiments, the compound comprises two or more residues of a contrast agent, wherein each residue of a contrast agent is covalently attached to a different arm of the multi-arm polymeric scaffold.

In certain embodiments, one arm of the multi-arm polymeric scaffold is covalently attached to the residue of biotin, and each of the remaining arms of the multi-arm polymeric scaffold is attached to a residue of a contrast agent.

In certain embodiments, the multi-arm polymeric scaffold comprises at least 3 arms. In certain embodiments, multi-arm polymeric scaffold comprises at least 4 arms or at least 6 arms.

In certain embodiments, the multi-arm polymeric scaffold comprises 8 arms. In certain such embodiments, the compound comprises 8 residues of a contrast agent.

In certain embodiments, the multi-arm polymeric scaffold comprises a hydrophilic polymer. Exemplary hydrophilic polymers useful in the compounds of the invention include polyacrylamide, polyurethanes, poly (hydroxyethyl methacrylamide), and polyethylene glycol. In certain embodiments, the multi-arm polymeric scaffold may be a multi-arm polyethylene glycol scaffold.

In certain embodiments, the contrast agent is a radiopaque contrast agent or pharmaceutically acceptable salt thereof. Exemplary contrast agents include diatrizoate, metrizoate, iothalamate, and ioxaglate. Preferably the contrast agent is ioxaglate.

In certain embodiments, the compound has the structure:

In certain embodiments, avidin and the one or more compounds are in a molar ratio of 1:4; and all four biotin-binding sites of avidin are bound to one of the one or more compounds.

In certain embodiments, the complex comprises four compounds described herein, wherein the four compounds are identical to each other.

In certain embodiments, the complex comprises four compounds described herein, wherein at least one compound is different from the other compounds.

In certain embodiments, the complex comprises four compounds described herein, wherein at least two compounds are different from each other and from the other compounds.

In certain embodiments, the complex comprises four compounds described herein, wherein all four compounds are different from each other.

The present invention further provides a method of diagnosing a joint disease, comprising administering to a subject a compound or a complex described herein; imaging the joint, and assessing the resultant images to determine whether the subject is suffering from a joint disease.

Exemplary joint diseases include rheumatoid arthritis, spondyloarthritis, juvenile idiopathic arthritis, lupus, gout, bursitis, and osteoarthritis. Preferably the method is a method for diagnosing osteoarthritis.

In certain embodiments, administering a compound or complex described herein comprises intra-articular injection.

In certain embodiments, the step of imaging comprises computed tomography (CT) imaging.

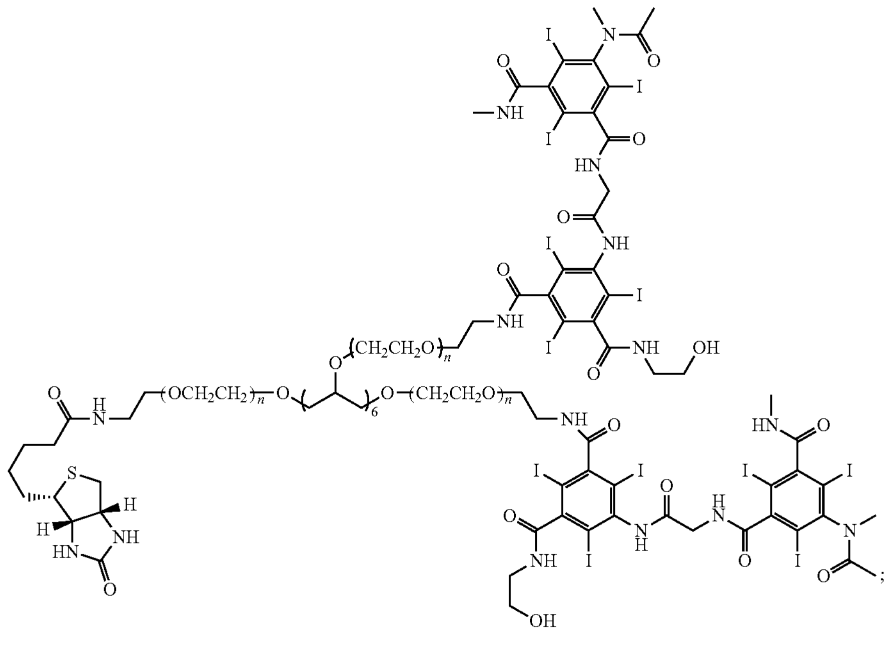

n is an integer from 1 to 500,000;

or a pharmaceutically acceptable salt thereof.

In further aspects, the present invention provides a complex comprising avidin and one or more compounds described herein. In certain embodiments, the one or more compounds are bound to avidin through electrostatic interactions.

The method also provides a method for imaging soft tissue, comprising administering to a subject a compound or a complex described herein, and imaging the soft tissue. In certain embodiments, the soft tissue is cartilage. In certain embodiments, the step of imaging comprises computed tomography (CT) imaging.

The present invention also provides a complex, comprising:

a cationic protein; and one or more residues of a contrast agent;

wherein the residue of the contrast agent is covalently attached to protein.

In certain embodiments, the cationic protein is avidin.

In certain embodiments, the contrast agent is a radiopaque contrast agent or pharmaceutically acceptable salt thereof. Exemplary contrast agents include diatrizoate, metrizoate, iothalamate, and ioxaglate. Preferably the contrast agent is ioxaglate.

The present invention further provides a method of diagnosing a joint disease, comprising administering to a subject a compound or a complex described herein; imaging the joint, and assessing the resultant images to determine whether the subject is suffering from a joint disease.

Exemplary joint diseases include rheumatoid arthritis, spondyloarthritis, juvenile idiopathic arthritis, lupus, gout, bursitis, and osteoarthritis. Preferably the method is a method for diagnosing osteoarthritis.

In certain embodiments, administering a compound or complex described herein comprises intra-articular injection.

In certain embodiments, the step of imaging comprises computed tomography (CT) imaging.

The method also provides a method for imaging soft tissue, comprising administering to a subject a compound or a complex described herein, and imaging the soft tissue. In certain embodiments, the soft tissue is cartilage. In certain embodiments, the step of imaging comprises computed tomography (CT) imaging.

Cationic Peptide Carriers for Cartilage Targeting

Targeted drug delivery to negatively charged tissues in the body such as cartilage remains an outstanding challenge. The high negative fixed charged density (FCD) of these tissues prevents effective diffusion of therapeutics to reach their target sites within the tissue. However, this high negative FCD can be utilized to enhance transport of therapeutics in such tissues through electrostatic interactions by making them positively charged. The concentration of positively charged carriers at the interface of negatively charged tissues is enhanced by a factor of $K^+$, known as Donnan partitioning coefficient compared to the surrounding bath of cationic solute ($K^+C$ vs C). This sharp increase in concentration of the cationic carrier at the tissue interface ($K^+C$) creates a higher concentration gradient along the tissue thickness which results in faster diffusion rates across the tissue. It is crucial to engineer the net positive charge of the carrier based on the negative FCD of the tissue to modulate the binding strength of the cationic carrier with the negatively charged tissue matrix to allow full thickness penetration using weak and reversible charge interactions. Too high of a positive charge will result in too strong binding that will hamper diffusion of the carrier into the tissue. Therefore, modulating the net positive charge of the carrier is essential to ensure full thickness penetration using weak reversible charge interactions, while the binding is strong enough to allow for high uptake and retention of the carrier in the tissue.

The present invention provides a charge based approach to modify therapeutic agents or contrast agents with optimally charged cationic peptide carriers (CPCs) for targeted delivery to a tissue of known fixed charge density (FCD). The invention is based in part on the surprising discovery of cartilage penetrating CPCs of varying net charge, spatial distribution and hydrophobicity (see table below) that enable delivery of a variety of macromolecules (including therapeutic drugs and contrast agents) inside cartilage. Studies presented herein and in *Acta Biomater.* (2018) doi:10.1016/j.actbio.2018.12.004 show that there exists an optimal charge range for a solute of given size to effectively target a tissue of known FCD.

Cationic peptide carrier (CPC) sequences and net charge

| Net charge (z) | Cationic Peptide Carrier Sequence | SEQ ID NO: |
|---|---|---|
| +8 | RRAAAARRAAAARRAAAARR | 1 |
| +14 | RRRRAARRRAARRRAARRRR | 2 |
| +16 | $(ARRRAARA)_4$ | 3 |
| +20 | RRRRRRRRRRRRRRRRRRRR | 4 |

As detailed in *Acta Biomater.* (2018) doi:10.1016/j.actbio.2018.12.004, CPC uptake increased with increasing net charge from +8 to +14. However, as charge increased further, the intra-cartilage penetration decreased likely due to stronger binding interactions that hindered CPC penetrability and uptake. This confirms that that weak-reversible binding is essential to enable penetration of CPCs through full tissue thickness.

In certain embodiments, CPC+8 is the carrier used for cartilage imaging due to its very fast transport rate, full depth penetration and shorter intra-tissue residence time, which can help clear contrast agents from the joint post imaging. The optimal charge of CPC+8 allows rapid transport in cartilage with short residence time which is ideal for delivery of imaging contrast agents. Additionally, upon incubation of CPC+8 with chondrocytes in culture, CPC+8 is not uptaken by the chondrocytes, which has clinical importance as for cartilage imaging purposes, presence of the contrast agents needs to be limited to the cartilage matrix rather than inside the cells.

CPC+14 had the highest intra-cartilage uptake among the CPCs, demonstrated high intra-cartilage retention while maintain full-thickness penetration. The optimal charge of CPC+14 allowed for stronger binding with cartilage GAGs without significantly reducing its transport rate. Consequently, the high uptake, high retention and full thickness diffusion of CPC+14 make it an ideal carrier for drug delivery applications. Thus, in certain embodiments, CPC+14 is the carrier used for delivering therapeutic agents to cartilage.

CPCs are shown to be safe for cell and cartilage matrix health with no harmful effects on rate of GAG loss, cell viability and rate of GAG synthesis by chondrocytes even at high concentrations (*Acta Biomater.* (2018) doi:10.1016/j.actbio.2018.12.004).

The present invention provides a method of delivering a contrast agent or an active pharmaceutical ingredient to a negatively charged tissue in a subject, comprising administering to the subject a complex;

wherein the complex comprises a residue of a contrast agent or an active pharmaceutical ingredient and a cationic peptide, wherein the peptide comprises from 2 to 40 amino acid residues, and the net charge of the peptide is from +7 to +20 inclusive; and the residue of the contrast agent or the active pharmaceutical ingredient is covalently bonded to the peptide.

In certain embodiments, the peptide comprises at least one arginine residue, lysine residue, or other positively-charged amino acid residue. In certain embodiments, the peptide comprises at least one arginine residue or lysine residue.

Exemplary peptides include:

```
                                        (SEQ ID NO: 1)
RRAAAARRAAAARRAAAARR;

                                        (SEQ ID NO: 2)
RRRRAARRRRAARRRRAARRRR;

                                        (SEQ ID NO: 3)
(ARRRAARA)4;
and

                                        (SEQ ID NO: 4)
RRRRRRRRRRRRRRRRRRRR.
```

In certain embodiments, the residue of the contrast agent or the active pharmaceutical ingredient is covalently bonded to the peptide at an arginine residue.

In certain embodiments, the peptide is RRAAAARRAAAARRAAAARR (SEQ ID NO: 1). In certain such embodiments, the complex comprises a residue of a contrast agent. Exemplary contrast agents include diatrizoate, metrizoate, iothalamate, and ioxaglate. In certain embodiments, the contrast agent is ioxaglate.

In certain embodiments, the peptide is RRRRAARRRRAARRRRAARRRR (SEQ ID NO: 2). In certain such embodiments, the complex comprises a residue of an active pharmaceutical ingredient. In certain embodiments, the active pharmaceutical ingredient is a protein such as IGF-1.

EXAMPLES

Materials 10 kDa 8-arm polyethylene glycol (PEG) amine hydrochloride salt was purchased from Advanced Biochemicals (Lawrenceville, GA). N-Hydroxysuccinimido (NHS)-biotin, 1-ethyl-3-(3 dimethylaminopropyl) carbodiimide hydrochloride (EDC), N-hydroxysulfosuccinimide (NHSS), Avidin and Avidin-Texas Red conjugated, 4'-hydroxybenzene-2-carboxylic acid (HABA), 3.5 kDa molecular weight cut-off (MWCO), 7.0 kDa MWCO SnakeSkin dialysis tubing was purchased from Thermo Fisher Scientific (Waltham, MA). Proteinase-K was purchased from Roche Diagnostics (Risch-Rotkreuz, Switzerland). Dulbecco's Modification of Eagle's Medium (DMEM) was from Cellgro (Manassas, VA). HEPES, non-essential amino acids (NEAA), penicillin-streptomycin Antibiotic-Antimycotic (PSA) and trypsin-EDTA phenol red were purchased from Gibco (Carlsbad, CA). Ascorbic acid and L-proline were from Fisher Bioreagents (Pittsburgh, PA). Propidium iodide (PI) was obtained from Thermofisher Acros Organics (Geel, Belgium). Human recombinant IL-1α was from PeproTech (Rocky Hill, NJ). Antibodies for type II collagen immunohistochemistry was acquired from the Developmental Studies Hybridoma Bank (University of Iowa), while the Vectastain Elite ABC kit was from Vector Laboratories (Burlingame, CA). Dex, SA, GA, PA, dimethyl sulfoxide-d6 (DMSO-d6) containing 0.03% (v/v) tetramethylsilane, fluorescein diacetate (FDA), fluorescein isothiocyanate isomer I (FITC), dimethylaminopyridine (DMAP), resazurin sodium salt, Griess reagent, histology reagents and other salts were purchased from Sigma-Aldrich (St. Louis, MO).

Chemical Synthesis

A. Biotinylation of 8-arm PEG 10 kDa PEG was biotinylated by reaction with NHS-biotin. Briefly, 10 mg (0.001 mmol, 1.0 equiv.) of PEG was dissolved in 500 μL of nanopure water and 1.7 mg (0.005 mmol, 5.0 equiv.) of NHS-biotin was dissolved in 500 μL of DMSO. NHS-biotin solution was then added dropwise to the PEG solution (5:1 molar ratio) and reacted for 2 h under gentle rotation at room temperature using click chemistry between the NHS group in biotin and amine groups in PEG. Excess NHS-biotin was removed from the PEG-biotin conjugate solution using dialysis (7.0 kDa MWCO) for 24 h against phosphate buffer saline (PBS). Extent of biotinylation was confirmed using the HABA dye assay [5, incorporated by reference].

B. Synthesis of Dexamethasone Hemisuccinate (Dex-SA), Glutarate (Dex-GA) and Phthalate (Dex-PA)

Three carboxylated derivatives of Dex were prepared by reacting 36.0 mg Dex (0.092 mmol, 1.0 equiv.) with 46 mg of SA, 52.0 mg of GA or 67.0 mg of PA (0.458 mmol, 5.0 equiv.) in presence of 2 mg DMAP (0.015 mmol, 0.2 equiv.) as a catalyzer in 1 mL of pyridine. The reaction for Dex-SA was conducted in a round bottom flask purged with nitrogen gas for 24 h at room temperature. For Dex-GA and Dex-PA, the reaction time was 48 h at 37° C. Following completion of the reaction, pyridine was evaporated with constant purging of nitrogen gas, and 4 mL of the cold solution containing 25 mL water and 10 mL concentrated hydrochloride acid (HCl) was added to the flask to precipitate Dex-SA, Dex-GA and Dex-PA out. A white precipitate was observed, which was stirred for 10 min and then centrifuged at 10,000 g for 5 min for 5 cycles. In each cycle, the supernatant was replaced with fresh cold solution of HCl. The final products of Dex-SA, Dex-GA, and Dex-PA were lyophilized, weighed and stored at −20° C. for future use. Their structures were confirmed using Proton Nuclear Magnetic Resonance ($^1$H-NMR). The carboxyl groups incorporated to the Dex were verified with thin layer chromatography (TLC).

C. Conjugation of Dex-SA, Dex-GA and Dex-PA to PEG-Biotin

Dex-SA was conjugated to PEG-biotin using EDC/NHS chemistry. Briefly, 5.0 mg of Dex-SA, Dex-GA or Dex-PA (0.010 mmol, 100.0 equiv.) was dissolved initially in 120 μL of DMSO and added 600 μL of 2-morpholinoethanesulfonic acid (MES) dropwise. Then, 19.2 mg of EDC (0.104 mmol, 104.0 equiv.) and 21.7 mg NHSS (0.092 mmol, 92.0 equiv.) were added to Dex-SA, Dex-GA and Dex-PA solution, and all of them were purged with nitrogen to activate the reaction for 30 min. Subsequently, 1.0 mg of PEG-biotin (0.100 μmol, 1.0 equiv.) was added to each of the solutions and reacted for 2 h at room temperature, purged with nitrogen gas. Upon completion of the reaction, the final product was dialyzed using 7.0 kDa MWCO membrane to remove the excessive reagents under 4° C. for 24 h. The pure product was then lyophilized and stored at −20° C. for future purposes. The formation of these three chemical compounds was then confirmed using $^1$H-NMR.

D. Conjugation of Ioxaglate (IOX) to PEG-biotin

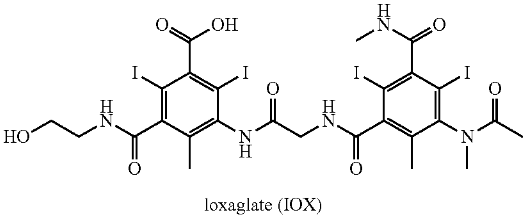

+

Ioxaglate (IOX)

-continued

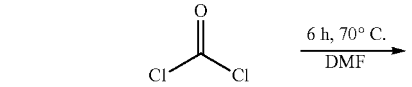

Thionyl chloride

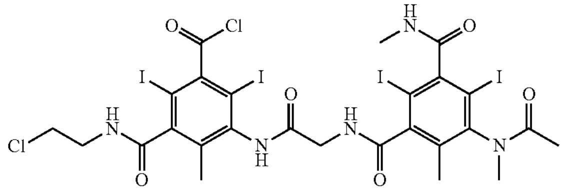

IOX-chloride (IOX-Cl)

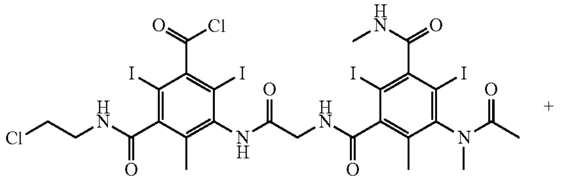

IOX-Cl

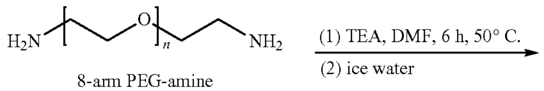

8-arm PEG-amine

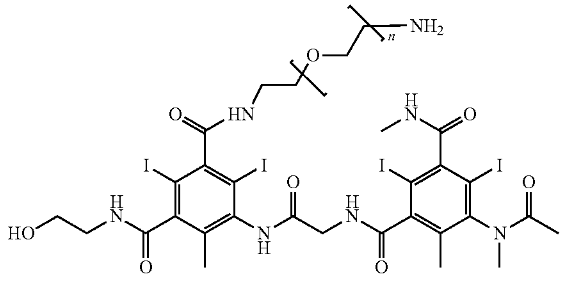

8-arm PEG-IOX

D1: Synthesis of Intermediate Product, Ioxaglate Chloride (IOX-Cl)

1. Weigh 12.7 mg of IOX (0.01 mmol, 20.0 equiv.) in 1.5 mL Eppendorf tube and suspend IOX with 110 μL thionyl chloride (1.5 mmol, 3000.0 equiv.) to form a gray insoluble mixture.
2. Add 5 μL DMF to mixture as a catalyst.
3. Purge nitrogen gas to remove any moisture inside the tube and use parafilm to seal tube cap.
4. Keep mixture reacting for 6 h at 70° C. using Thermal Shaker, with 600 rpm shaking speed. IOX will dissolve at high temperature producing a brown solution.
5. After the reaction, cool down the synthesized intermediate product (IOX-Cl). To remove excessive unreacted thionyl chloride, keep the product under vacuum at 20° C. Intermittent slight heating of thionyl chloride to 40° C. will also facilitate its evaporation. To protect the vacuum pump, thionyl chloride vapor should pass through a gas washing bottle containing 1 N NaOH solution.
6. Add 200 μL DMSO to dissolve the remaining solid and transfer the solution to a new 1.5 mL Eppendorf tube for lyophilization.
7. Dissolve 5 mg of standard IOX and IOX-Cl in 700 μL DMSO-d6 for 1H-NMR, respectively. The structure of IOX-Cl can be verified using 500 MHz $^1$H-NMR. The disappearance of hydroxyl peak and carboxyl peak in IOX-Cl compared to the IOX standard, confirms that hydroxyl and carboxyl groups of IOX have been chloritized.

D2: Conjugation of IOX-Cl to 8-Arm Biotin-PEG to Synthesize Biotin-PEG-IOX

1. Synthesize biotinylated 8-arm PEGs as outlined in section A, above.
2. To conjugate IOX-Cl to 8-arm biotin-PEG, first dissolve 13.1 mg of the lyophilized product, IOX-Cl (0.01 mmol, 20 equiv.) in 300 μL of anhydrous DMF using 1.5 mL Eppendorf tube.
3. Add 7.5 μL TEA dropwise to the solution from step 2. Keep this solution at 4° C. using a Thermal Shaker.
4. Dissolve 5.5 mg of 8-arm biotin-PEG in 100 μL DMF (0.0005 mmol, 1 equiv.) to make 8-arm biotin-PEG solution. Then, add it dropwise to the IOX-Cl solution from step 3.
5. Conduct this reaction in Thermal shaker at 4° C., 600 rpm for 30 min and then at 50° C., 600 rpm for 16 h.
6. After the reaction, transfer the reacted product (8-arm biotin-PEG-IOX) to 4 mL ice-water in order to precipitate unreacted IOX-Cl. Centrifuge the mixture at 10,000 g for 5 min and collect the supernatant.
7. To further purify the product, add collected supernatant to 3.5 kDa dialysis membrane and then dialyze against PBS for 24 h and DI water for another 24 h at room temperature.
8. Then lyophilize the purified product, 8-arm biotin-PEG-IOX and freeze at −80° C. for future applications.
9. To estimate the amount of IOX loaded on 8-arm biotin-PEG, use HPLC equipped with a Variable Wavelength Detector and an Advance Bio RP-mAb C4 4.6×150 mm column. Prepare a gradient of solvent A (0.1% TFA in water) and solvent B (0.1% TFA in acetonitrile). Linearly increase the concentration of solvent B from 5% to 65% over 26 min. Set column temperature at 45° C. and a flow rate of 1.0 mL/min. Standard IOX will elute at 3.710 min, and 8-arm biotin-PEG-IOX will be eluted between 18 to 24 min (254 nm) as PEG polymer does not have constant repeating units and the amount of IOX is not conjugated evenly to PEG. Estimate the total UV absorbance (mAU*s) of PEG-IOX by integrating the area under the curve and then estimate IOX concentration according to IOX standard curve. About an average of 3.82±0.50 moles of IOX conjugated to one mole of 8-arm biotin-PEG is expected.
10. Use MALDI-TOF to confirm the increase in molecular weight of 8-arm biotin-PEG-IOX compared to 8-arm biotin-PEG. Each mole of 8-arm biotin-PEG is conjugated to 2.33 moles of IOX on an average.

E. Loading of Dex-PEG-Biotin on Avidin to Synthesize mAv-Dex

The three Dex-PEG-biotin products from section C, above, were reacted with Avidin in nanopure water for 30 min under gentle shaking at room temperature in 1:1, 2:1, 3:1, 4:1, 5:1, 6:1 and 8:1 molar ratios to determine the ratio at which all four biotin binding sites of Avidin are occupied by Dex-PEG-biotin to form 1:4 mAv, which was confirmed using the HABA dye assay. For subsequent drug release and biological studies, we have used 1:4 mAv configuration as it has higher number of sites for drug loading than 1:2 mAv and it has been referenced simply as mAv in following text. In one formulation, mAv-Dex-SA, mAv-Dex-GA, and mAv-Dex-PA were physically mixed together in 2:1:1 molar ratio of Dex, abbreviated as controlled release mAv-Dex (2:1:1). We compared its bioactivity with mAv-Dex-SA, which is referred as fast release mAv-Dex throughout the manuscript. The products were then lyophilized and stored at −20° C. until further use.

F. Loading of Biotin-PEG-IOX on Avidin to Synthesize mAv-IOX

Biotin-PEG-IOX from Section D may be reacted with Avidin according to the method outlined in Section E.

Application in Computed Tomography of Cartilage

Figure 9:
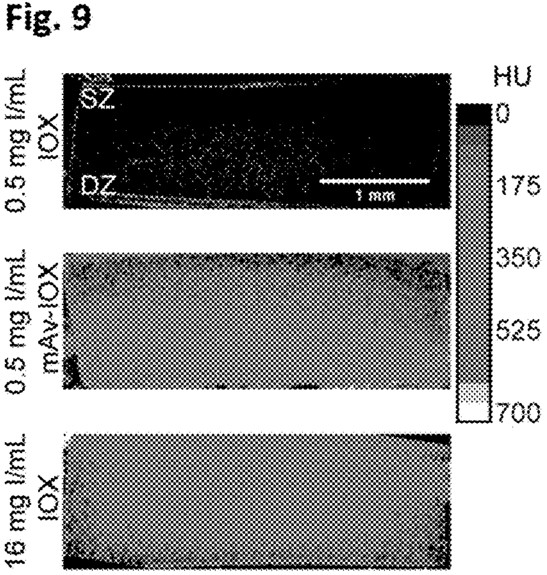
FIG. 9 is a 2D color map of cartilage treated with 0.5 mg I/mL IOX, 16 mg I/mL IOX and 0.5 mg I/mL mAv-IOX. 0.5 mg I/mL mAv-IOX produces high CECT attenuation than 0.5 I/mL IOX and shows similar CECT attenuation to 16 mg I/mL IOX.

1. Use the procedure in Section F to conjugate 4 moles of biotin-PEG-IOX with Avidin at its biotin binding sites to synthesize mAv-IOX.
2. Use Zetasizer Nano-ZS90 to detect the zeta potential of unmodified Avidin and mAv-IOX in DI water; the zeta potential (Q, mV) of Avidin and mAv-IOX should be around 18.3±0.5 mV and 8.69±0.7 mV, respectively.
3. Obtain 3 mm diameter×1 mm height cylindrical cartilage discs with intact superficial zone (SZ) from femoropatellar grooves of 1-2-week-old bovine knee joints and freeze them in PBS containing protease inhibitors (PI) until further use.
4. Prepare (A) 0.5 mg I/mL IOX solution; (B) 16 mg I/mL IOX solution; (C) 0.5 mg I/mL mAv-IOX solution using PBS/PI (dissolve 1 tablet PI in 50 mL PBS buffer) as solvent. Use a freezing point osmometer to balance the osmolality of these contrast agent solutions to 400±20 mOsm/kg by adding 1 M sodium chloride solution dropwise.
5. Incubate 3 mm diameter cartilage explants in 96-well plate with 300 μL of different iodinated contrast agent solutions (0.5 mg I/mL IOX; 16 mg I/mL IOX and 0.5 mg I/mL mAv-IOX) for 24 h at 37° C. using an incubator.
6. Secure cartilage explants using low X-ray-absorption foam inside a 20.5 mm CT scan tube. Ensure that the cartilage explant stays secured in the foam during CT imaging.
7. Take one of the equilibrated cartilage explants from contrast agent solution and gently using Kimwipes to remove solution from the tissue surface.
8. Set CT35 with an isotropic voxel resolution of 10 μm, 70 kVp tube voltage, 113 μA current, and 200 ms integration time method. The CT data will be saved as DICOM format. ImageJ software will automatically display Hounsfield Unit (HU) by importing DICOM images.
9. Process the CT imaging data acquired from CT35 using ImageJ software: (i) Go to Image→Stacks→Images to Stack to convert CT imaging data to a cartilage stack. (ii) Go to Image→Stacks→Reslice and select ‘starting at top’ to acquire a new stack showing vertical section of cartilage from superficial zone (SZ) to deep zone (DZ). The output spacing (mm) is 0.010 and select ‘Avoid interpolation’. (iii) Go to Image→Adjust→Threshold and apply range as −300 to +∞. Any intensities below −300, which is mostly background, will be set to ‘NaN’. (iv) Use an ImageJ plugin (use the link in Note 8) to acquire Z-projection of average intensity of the cartilage stack. The cartilage stack will be converted to one image with average intensity. (v) Go to LUT→16 colors to create a color map of cartilage. (vi) Go to Image→Adjust→Brightness/Contrast and set 0 minimum and 700 Maximum to show higher contrast among different intensities in cartilage color map. (vii) Go to Analyze→Tools→Calibration Bar to add a calibration color bar.
10. The color maps of contrast agent spatial distributions in cartilage explants from SZ to DZ are shown in FIG. 9. 0.5 mg I/mL mAv-IOX produced significantly high CECT attenuation with intensity increasing with GAG density from SZ to DZ of cartilage. Similar IOX concentration did not show any signal and 32× high concentration of IOX (16 mg I/mL) was needed to produce similar CT attenuation.

Estimating Correlation Between Contrast Enhanced CT Attenuation (CECT) and GAG Density in Cartilage 1. Incubate 3 mm diameter cartilage explants in 96-well plates with saline as blank control, 0.1 U/mL chondroitinase-ABC for 8 h and 16 h, 0.25 U/mL chondroitinase-ABC for 16 h and 24 h in order to induce varying degrees of GAG depleted cartilage to simulate different OA stages (early, mid and late stage). After digestion of chondroitinase-ABC, wash each cartilage with PBS/PI for 3 times.
2. Incubate these explants in 0.5 mg I/mL mAv-IOX and 16 mg I/mL IOX to enhance CT imaging of these cartilages using same CT imaging procedure above.
3. Calculate mean attenuation of every slice in cartilage stack using ImageJ software: (i) Draw a region of interest (ROI) of cartilage and keep ROI same between different cartilage slices. (ii) Go to Image→Adjust→and set range as −300 to +∞. Any intensity below −300 will be set to ‘NaN’. (iii) Go to Image→Stacks→Measure Stack to acquire the mean attenuation of each slice. (iv) The average of the mean attenuation of all the cartilage slices is used as mean CECT attenuation of cartilage.
4. After CT imaging, digest each cartilage using 1 mL of 1 mg/mL protease K for 48 h at 57° C. Vortex each vial properly and measure the total residual glycosaminoglycans (GAGs) in digested explants using the DMMB assay. The GAG content (mg/mg wet weight) is calculated as:

$$GAG\ \text{content} = \frac{\text{Total residual } GAGs\ (\text{mg})}{\text{Wet weight of cartilage (mg)}}$$

Figure 10A:
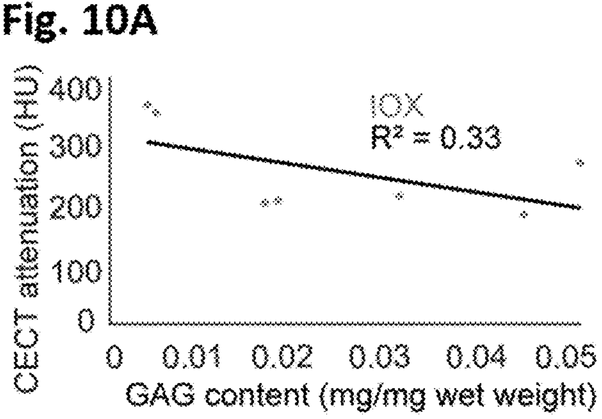
FIG. 10A contains graphs showing the correlation between CECT attenuation and GAG content of cartilage using 16 mg I/mL IOX.
Figure 10B:
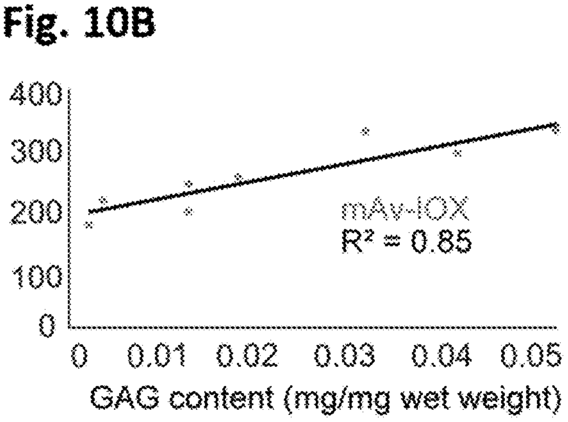
FIG. 10B contains graphs showing the correlation between CECT attenuation and GAG content of cartilage using 0.5 mg I/mL mAv-IOX.

5. Build up the correlation graph between CECT mean attenuation and GAG content in cartilage (total GAG concentration per unit wet weight of cartilage) as showed in FIGS. 10A and B. A strong positive correlation between mAv-IOX CECT attenuation and residual GAG content in cartilage explant should be observed indicating the high potential of cationic contrast agent, mAv-IOX, in diagnosing different stages of OA.

Analysis

Degree of Biotinylation Using HABA Colorimetric Assay

The extent of biotinylation of PEG and the loading of PEG-biotin on Avidin were determined by using the HABA colorimetric assay [5]. Changes in absorbance of the HABA-Avidin complex at 500 nm due to competitive displacement by the biotinylated PEG was used to estimate the degree of biotinylation. HABA dye was dissolved in 10 mL of nanopure water (2.42 mg/mL) and filtered using 0.2 μm filter. Excessive HABA dye was added to Avidin solution to a final concentration of 0.82 mg/mL (initial absorbance of 1.2). 20 μL of graded concentrations of PEG-biotin or Dex-PEG-biotin were added to 180 μL of HABA-Avidin complex (1:1 through 8:1 molar ratio of PEG-biotin to HABA-Avidin) that competitively displaced HABA from the biotin binding sites of Avidin thereby reducing the absorbance value. 100% PEGylation of Avidin was achieved when the change in absorbance achieved a plateau.

Gel Electrophoresis

Conjugation of PEG-biotin to Avidin was confirmed by using native polyacrylamide gel electrophoresis (PAGE) in 7.5% separating gel. In brief, 12 μL of protein samples (~7.5 μg protein) in DI water were mixed with 4 μL of 2× Native Tris-Glycine sample loading buffer without heating. Since the isoelectric point of Avidin is 10.5 and the protein mobility depends on both the charge and molecular weight in the native PAGE gel, the electrode polarity had to be reversed (anode was inserted at the top of gel and cathode was inserted at the bottom of gel). Electrophoresis was performed for approximate 4 h in 1× solution of non-sodium dodecyl sulfate tris-base running buffer at 200 V, 40 mA and 4° C.

Native gel was stained using iodine solution and Coomassie Brilliant Blue R-250. Gel was fixed and then washed with deionized (DI) water for 20 min. Gel was then incubated in 5% barium chloride solution for 15 min followed by 3 washes in DI water. Subsequently, the gel was stained with potassium iodide and iodine solution for 5 min to identify free or conjugated PEG. Following this, the gel was stained with Coomassie Brilliant Blue R-250 for Avidin, and de-stained three times in 100 mL of 10% acetic acid solution for 1 h.

Ultra Performance Liquid Chromatography (UPLC) and Zeta Potential

PEGylation of Avidin in 1:2 and 1:4 mAv was further confirmed by using H-Class Acquity UPLC (Waters Corp, Milford, MA) equipped with an Acquity UPLC BEH200 Size Exclusion Column (200 Å, 1.7 μm column, 4.6×300 mm) with 20 mM ammonium bicarbonate buffer as the mobile phase at 0.2 mL/min. Avidin was detected at 280 nm. Zeta potential of Avidin and mAv was measured in nanopure water at 0.45 mg/mL concentration using a Zetasizer Nano-ZS90.

Proton Nuclear Magnetic Resonance ($^1$H-NMR)

Modification of Dex and conjugation of Dex-SA, Dex-GA, Dex-PA to PEG-biotin were verified using 500 MHz $^1$H-NMR (Varian Inova. Agilent Technologies). 1-2 mg of solutes to be tested were dissolved in 700 μL DMSO-d6. In addition, $^1$H-NMR spectra of Dex-SA, Dex-GA, Dex-PA reacted with PEG-biotin using EDC/NHS chemistry were also confirmed. The obtained NMR data was analyzed using MestRe Nova software.

Dex Loading Content

Dex-PEG-biotin was hydrolyzed using 0.1 N hydrochloric acid overnight and neutralized against 0.1 N sodium hydroxide. The amount of Dex released was quantified by HPLC (Agilent Technologies 1260 infinity II) equipped with a Variable Wavelength Detector using a Poroshell 120 EC-C18 4.6×150 mm column. A gradient of solvent A (0.1% trifluoroacetic acid (TFA) in water) and solvent B (0.1% TFA in acetonitrile) was used. The concentration of solvent B was increased linearly from 5% to 65% over 15 min. Column temperature of 30° C. and a flow rate of 1.0 mL/min were used. Dex was detected at 254 nm. Drug loading content (DLC) was calculated as:

$$DLC = \frac{\text{Total Dex encapsulated } (g)}{\text{Total Dex encapsulated } (g) + \text{Mass of Avidin } (g)} \quad (1)$$

In-Vitro Dex Release Rates

Dex release rates from Dex-PEG-biotin were estimated in PBS at pH 7.4, 37° C. using dialysis tubing (7.0 kDa MWCO) with continuous shaking under sink conditions: Dex concentration was kept 10× lower than the saturation solubility of Dex in PBS. At different time intervals, 200 μL of release media was used to estimate the Dex concentration by HPLC, which was replaced by equal amount of fresh release media.

Transport Studies

Equilibrium Uptake of mAv in Cartilage

Cartilage explants were harvested from the femoropatellar groove of 2-3-week-old bovine knees (Research 87, Boylston, MA) with a 3 mm diameter biopsy punch. The cylindrical plugs were then sliced to obtain the superficial 1 mm layer of cartilage, and frozen until use. Dual labeled mAv was synthesized by conjugating Texas Red labeled Avidin with FITC labeled 8-arm PEG. Cartilage disks were equilibrated in 300 μL of 8.5 μM of labeled Avidin, 1:2 mAv or 1:4 mAv in presence of protease inhibitors for 24 h in a 96-well plate at 37° C. on gentle shaking to prevent formation of stagnant layers. To minimize evaporation, the empty wells in the plate were filled with DI water and the plate was wrapped in parafilm. At the end of the experiment, the surfaces of each disk were quickly blotted with Kimwipes and the wet weight was measured. The equilibrium bath fluorescence was measured using a plate reader (Synergy H1, Biotek). The final concentration was calculated based on a linear calibration correlating fluorescence to concentration of labeled Avidin. The moles of solutes absorbed into the cartilage were calculated using the difference between the initial and equilibrium concentration of the bath. The concentration of solutes inside was calculated by normalizing the number of moles inside cartilage to the wet weight of the tissue. The uptake ratio (Ru) was defined as the ratio of the concentration of solutes inside the tissue ($C_{tissue}$) to that of the solute in the equilibrium bath ($C_{bath}$).

$$R_U = \frac{C_{tissue}}{C_{bath}} \quad (2)$$

To measure uptake of labeled Avidin and mAv in partially-degraded tissue modeling osteoarthritic cartilage, cartilage explants were incubated in 0.10 mg/mL trypsin-EDTA phenol red solution in PBS for 5 h, which induced about 50% GAG depletion [1]. GAG content in cartilage was measured using the dimethyl-methylene blue (DMMB) assay [6]. The explants were then rinsed multiple times and incubated in PBS containing protease inhibitors for 1 h to wash out trypsin before using for uptake experiments.

Confocal Imaging to Estimate Depth of Penetration into Cartilage

A previously described transport setup was used to study 1-dimensional diffusion of solutes in cartilage. Briefly, 6 mm half disk cartilage explants were mounted in the mid-section of the chamber. The upstream compartment was filled with either 9.5 μM of labeled Avidin or dual labeled 1:2 and 1:4 mAv. The transport chamber was placed in a petri-dish containing water to minimize evaporation and placed on a shaker inside an incubator at 37° C. After 24 h of adsorption, a 100 μm slice was cut from the center of the explant and imaged using a confocal microscope (Zeiss LSM 700). Texas Red was excited using 555 nm laser line and FITC was separately excited using 488 nm laser line. Z-stack multilayer image of both channels (Red and Green) were obtained to visualize distribution of mAv conjugates. The maximum intensity of each channel was projected to the Z-axis.

Intra-Cartilage Diffusion Kinetics

A custom designed transport chamber made out of transparent poly (methyl methacrylate) was used to measure non-equilibrium one-dimensional diffusion of solutes in cartilage as described previously [1]. The interior walls of the transport chamber were equilibrated in 0.5% nonfat-dried bovine milk solution in PBS for 15 min to lessen non-specific binding of solutes to inner walls of the transport chamber. Subsequently, the compartments of chamber were rinsed with DI water. 3 μM solution of labeled Avidin or mAv was added to the upstream chamber. A 6 mm diameter cartilage disk of 400-600 μm thickness was placed between the upstream and downstream compartments. Concentration of fluorescently labeled solutes in the downstream chamber was measured over time by exciting the downstream solution using a 480 nm laser line and detecting the emission. Non-equilibrium diffusion curves were thereby obtained by plotting normalized downstream concentration ($C_D$) to upstream concentration (Cu) over time. Effective Diffusivity ($D_{EFF}$), which is the diffusivity of solutes in cartilage while binding interactions exist within the tissue was estimated as follows:

$$\tau_{Lag} = \frac{L^2}{6D_{EFF}} \quad (3)$$

where L corresponds to cartilage thickness, and $\tau_{Lag}$ is the time it takes to reach a steady state flux. $\tau_{Lag}$ was estimated using the time-axis intercept of the linear slope of the normalized concentration versus time.

In-Vitro Cartilage Explant Culture Model of OA 3 mm diameter cartilage explants harvested from calf knee joints were equilibrated separately in serum free culture media containing 96.2% low-glucose DMEM, 1.0% HEPES, 1.0% NEAA, 1.0% PSA, 0.4% proline and 0.4% ascorbic acid for 48 h at 37° C., 5% $CO_2$ for 2 days prior to treatment. Tissue explants for all treatment conditions were matched for depth and location to prevent any bias. To test the biological effectiveness of mAv-Dex, equilibrated cartilage explants were treated with or without IL-1α (2 ng/mL) for 16 days in combination with (i) a single dose of 100 nM free Dex, (ii) a continuous dose of 100 nM free Dex, (iii) a single dose of 10 μM free Dex (iv) a single dose of fast release mAv-Dex (10 μM Dex) or (v) a single dose of controlled release mAv-Dex (2:1:1) (10 μM Dex). To evaluate the effect of mAv carrier alone on cartilage health, a high one-time dose of 10 μM mAv, which is 10× higher than that used to deliver 10 μM Dex in condition (v) above, was also tested in the absence of IL-1α. Note that mAv here refers to 1:4 mAv configuration. Media was changed every 2 days and IL-1α was replenished at each medium change. Single dose treated explants were subjected to the drug and its carrier for only the first 2 days; in the following media changes, the media did not contain the drug, thereby simulating a single intra-articular injection in-vivo [4]. In the continuous dosing condition, Dex was replenished throughout the culture duration. IL-1α concentration was chosen as it represents a moderately aggressive cytokine treatment. Previous work has shown that a sustained (continuous) dosing of 10-100 nM Dex throughout the culture duration is effective in suppressing cytokine induced catabolism [4]; we, therefore, compared single and continuous dosing with 100 nM free Dex. Single dose of mAv-Dex with effective Dex concentration of 10 M was chosen for intra-cartilage drug depot delivery to provide a sustained drug dose of at least 10 nM Dex throughout the culture duration and compared with the equivalent concentration of free Dex.

GAG Loss and Nitrite Release from Cartilage

After 16 days of culture, cartilage explants were weighed and digested in proteinase K. The cumulative GAGs released to the media and residual GAGs in the digested explants were measured using the DMMB assay [6]. Nitrite content was measured using the Griess assay as an indicator of nitric oxide (NO) release from tissues. Equal volumes of Griess reagent and culture media collected every two days were mixed and incubated at room temperature for 15 min, and absorbance at 540 nm was measured using a plate reader. Sodium nitrite was used as a standard.

Chondrocyte Viability and Metabolism

Chondrocyte viability was analyzed by staining cartilage explants with FDA (4.0 mg/mL) and PI (10.0 mg/mL) for live (green) and dead (red) cells, respectively. Slices were washed with PBS and imaged at 4× magnification (Nikon Eclipse Ts2R). The live and dead images were overlaid using ImageJ. At the end of the culture, tissue explants were incubated with media containing 1× resazurin sodium salt (alamarBlue assay) for 3 h in dark at 37° C. and 5% $CO_2$. Cell metabolic activity was estimated by measuring fluorescence at 530 nm excitation and 590 nm emission wavelengths.

Histology and Immunohistochemistry

Cartilage explants were fixed in 4% formalin, embedded in 0.75% agarose for ease of handling, dehydrated in a graded series of ethanol and xylenes, and embedded in paraffin. Transverse sections (to obtain full thickness cartilage slices with superficial and deep zones) were taken at 5 μm thickness. These sections were stained with 0.5% Safranin O, 0.02% Fast Green and Weigert's iron hematoxylin for GAG detection. Adjacent sections underwent antigen retrieval using 0.1% hyaluronidase, 0.1% pronase in PBS for 30 min at 37° C., then were immunostained for type II collagen using 1 μg/mL mouse IgG1 (clone II-II6B3) or normal mouse IgG1 as isotype control. Antibody detection was performed using a VectaStain Elite ABC kit with 3,3-diaminobenzidine staining. Stained sections were imaged using a Zeiss Axioplan2 equipped with an AxioCam HRc camera.

Statistical Analysis

Data is presented as Mean±Standard Deviation. For all studies, n=6-8 explants per condition and experiments were repeated using explants from at least 3 animals. A general linear mixed effects model was used with animal as a random variable. For comparisons between different treatment conditions, Tukey's Honestly Significant Difference test was used. P<0.05 was considered statistically significant.

Results

Synthesis and Characterization of mAv

Figure 11A:
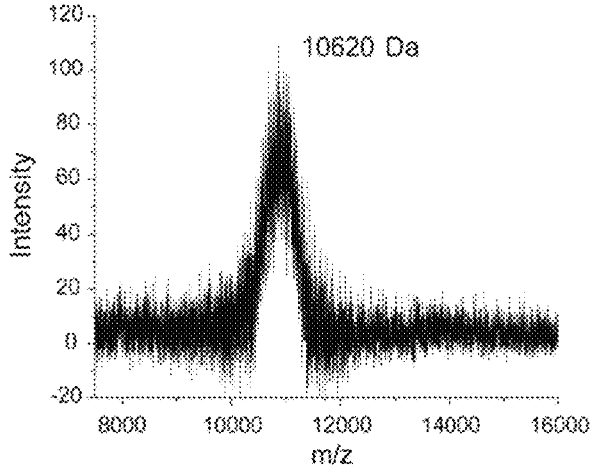
FIG. 11A shows a graph confirmation of PEG.
Figure 11B:
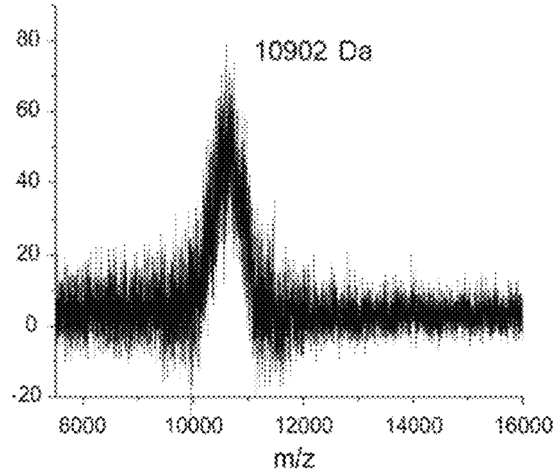
FIG. 11B shows a graph confirmation of biotinylated PEG using MALDI-TOF MS. The calculated mass of PEG is 10620 Da and biotinylated PEG is 10902 Da.
Figure 12A:
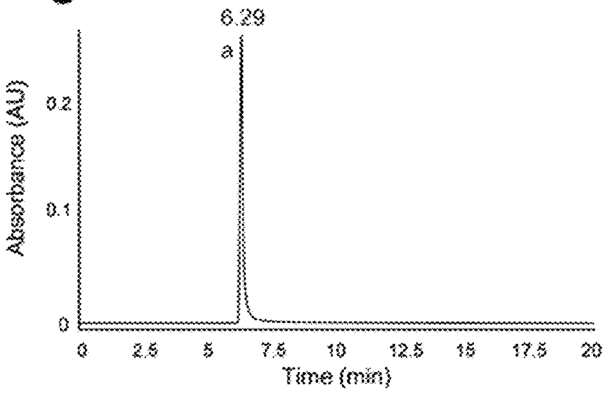
FIG. 12A shows UPLC analysis of native Avidin.
Figure 12B:
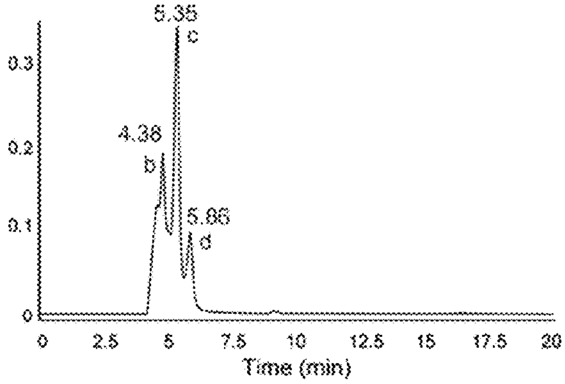
FIG. 12B shows UPLC analysis of 1:2 mAv: Peak 'a' for Avidin is at 6.29 min, peak 'b' for mAv with three PEGs is at 4.38 min, peak 'c' for mAv with two PEGs is at 5.35 min and peak 'd' for mAv with one PEG is at 5.86 min.
Figure 13A:
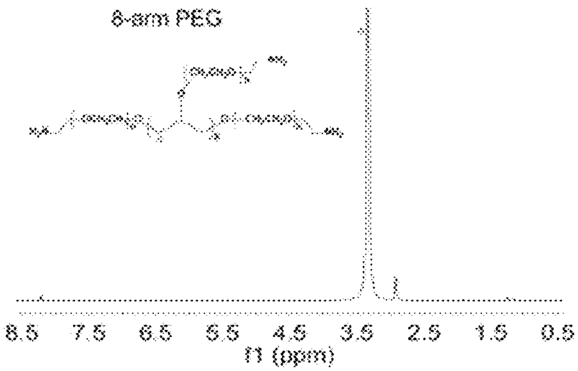
FIG. 13A shows the $^1$H NMR spectrum of 8-arm PEG in Dimethyl sulfoxide-d6. The lower-case labels "a~i" indicate the resonance peaks corresponding to each proton in the structure.
Figure 13B:
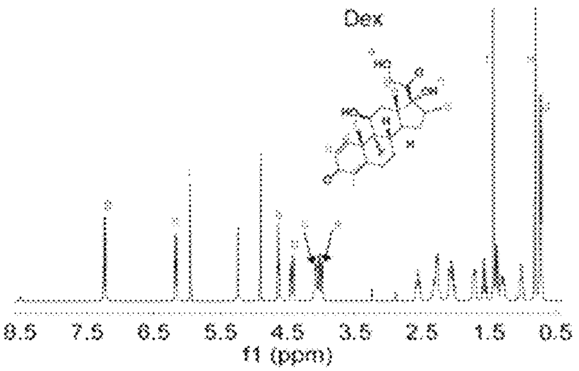
FIG. 13B shows the $^1$H NMR spectrum of Dex in Dimethyl sulfoxide-d6. The lower-case labels "a~i" indicate the resonance peaks corresponding to each proton in the structure.
Figure 13C:
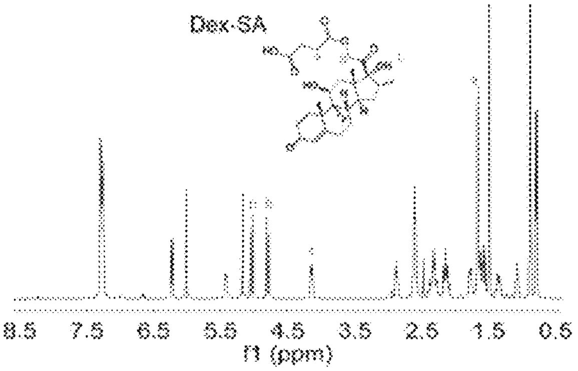
FIG. 13C shows the $^1$H NMR spectrum of Dex-SA in Dimethyl sulfoxide-d6. The lower-case labels "a~i" indicate the resonance peaks corresponding to each proton in the structure.
Figure 13D:
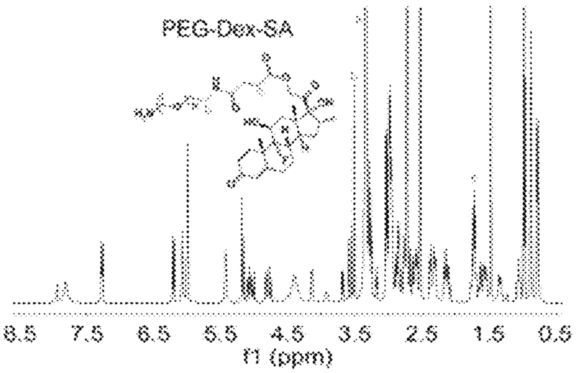
FIG. 13D shows the $^1$H NMR spectrum of PEG-Dex-SA in Dimethyl sulfoxide-d6. The lower-case labels "a~i" indicate the resonance peaks corresponding to each proton in the structure.
Figure 13E:
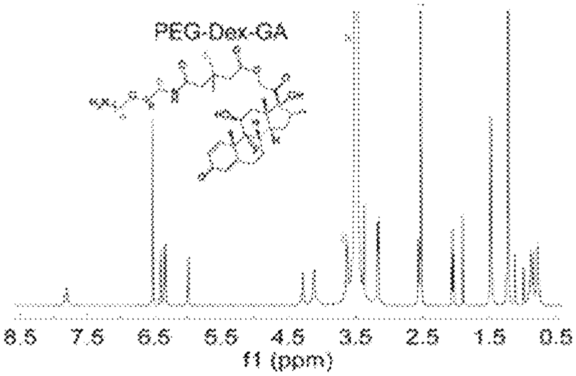
FIG. 13E shows the $^1$H NMR spectrum of PEG-Dex-GA in Dimethyl sulfoxide-d6. The lower-case labels "a~i" indicate the resonance peaks corresponding to each proton in the structure.
Figure 13F:
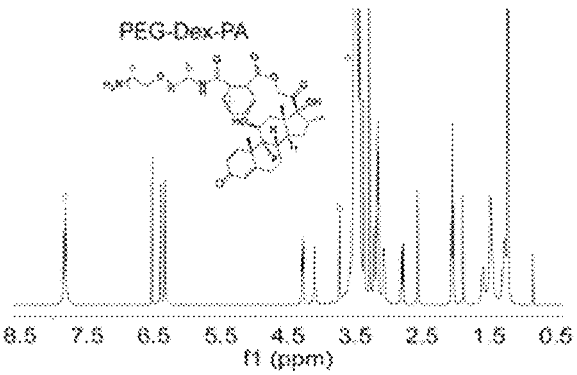
FIG. 13F shows the $^1$H NMR spectrum of PEG-Dex-PA in Dimethyl sulfoxide-d6. The lower-case labels "a~i" indicate the resonance peaks corresponding to each proton in the structure.

The 1:5 molar ratio of PEG to NHS-biotin was optimal for synthesizing biotinylated 8-arm PEG using NHS ester reaction chemistry, resulting in every molecule of PEG being conjugated with one molecule of biotin as confirmed by matrix-assisted laser-desorption ionization time-of-flight mass spectrometry (MALDI-TOF MS) (FIG. 11A-11B); PEG MW was estimated as 10620 Da which increased to 10902 Da following biotinylation showing that on an average 1.15 biotin per PEG were present. In addition to the mass spectrometry data, degree of biotinylation was also confirmed by using the HABA dye assay where the addition of biotinylated PEG to the HABA-Avidin complex displaced the HABA dye and reduced the absorbance value. Using the Beer-Lambert Law [5], an average of 1.28±0.02 biotin per PEG molecule was estimated, which is consistent with the mass spectrometry data.

Figure 2A:
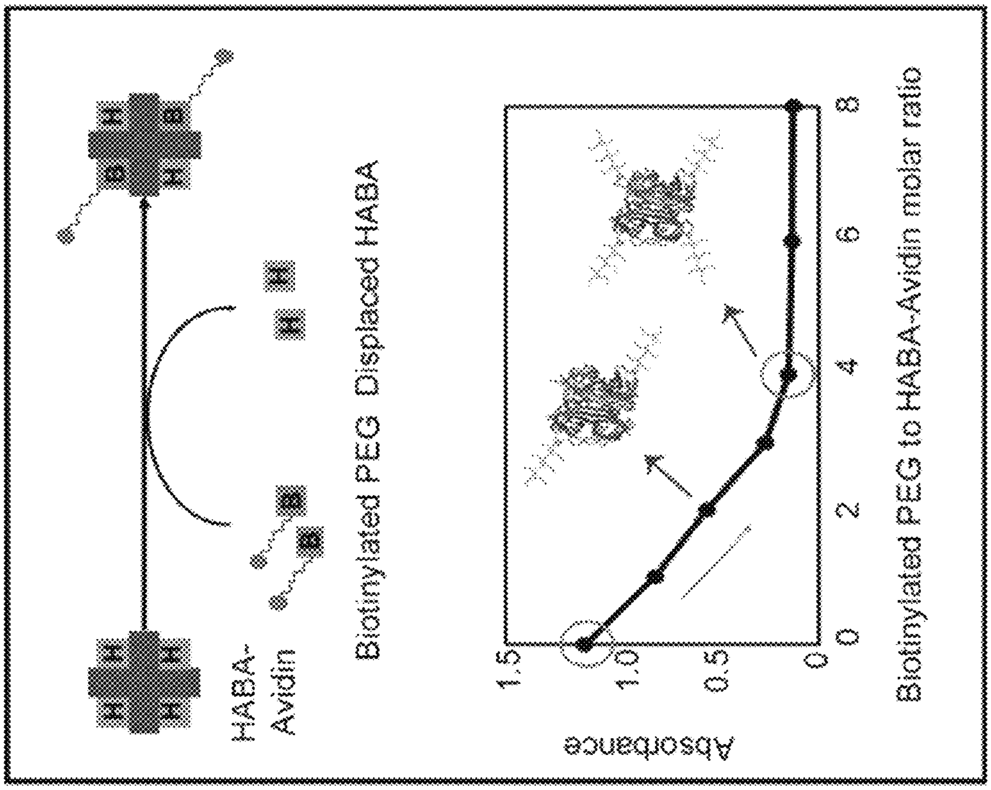
FIG. 2A depicts the characterization of multi-arm Avidin (mAv) synthesis. Schematic of HABA dye assay: HABA binds with Avidin resulting in a high absorbance value but is competitively displaced by biotin or biotinylated PEG reducing the absorbance value. (Bottom) Titration curve of biotinylated PEG with HABA-Avidin mixture. Absorbance value dropped with increasing biotinylated PEG:HABA-Avidin molar ratio, and a plateau was achieved after 4:1 molar ratio confirming that all four binding sites of Avidin (Av) were occupied by PEGs to form 1:4 mAv configuration.
Figure 2B:
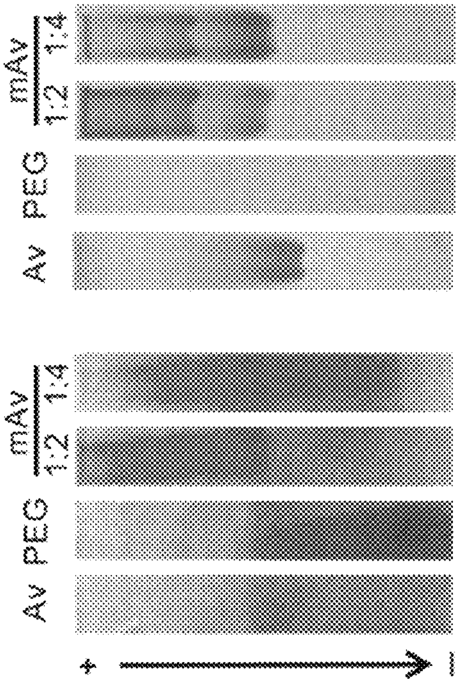
FIG. 2B depicts the characterization of multi-arm Avidin (mAv) synthesis. Native PAGE gel (7.5%) of Av, PEG, 1:2 mAv and 1:4 mAv under reverse polarity stained with (left) iodine for PEGs and with (right) Coomassie Brilliant Blue R-250 for protein.

PEGylation in mAv was confirmed using the HABA dye assay, gel electrophoresis and UPLC. FIG. 2A shows the reduction in absorbance value with increasing molar ratio of biotinylated PEG to HABA-Avidin from 1:1 to 4:1, following which a plateau is achieved meaning that a majority of biotin sites on Avidin were occupied by PEG-biotin indicating the formation of 1:4 mAv. FIG. 2B shows native PAGE gel in reverse polarity used to confirm PEGylation in 1:2 and 1:4 mAv containing two or four 8-arm PEGs, respectively. PEG is stained as yellow with iodine and protein is stained as blue with Coomassie Brilliant Blue R-250. In PEG-staining (left), bands only appear in the PEG and mAv channels. However, in protein-staining (right), bands only appear in the Avidin and mAv channels. Therefore, bands at the same position in the mAv channels with both PEG-staining and protein-staining verified the formation of mAv.

Figure 2C:
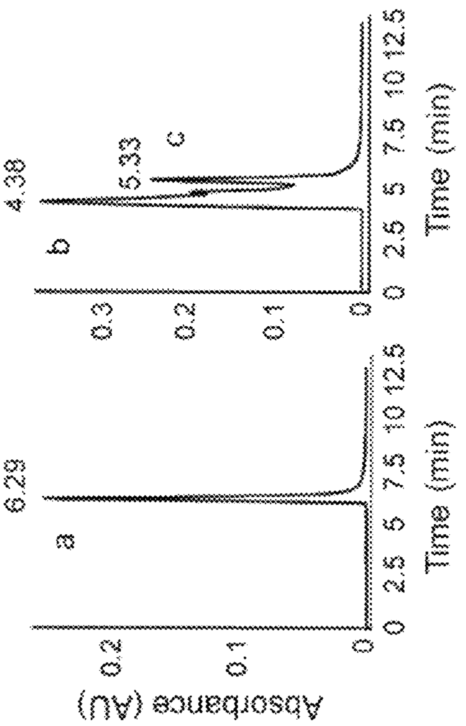
FIG. 2C depicts the characterization of multi-arm Avidin (mAv) synthesis. UPLC analysis of (left) native Av with peak 'a' at 6.29 min and (right) of 1:4 mAv formulation containing a majority of mAv with 4 PEGs (peak 'b' at 4.38 min) and a secondary population of mAv with 2 PEGs (peak 'c' at 5.33 min).

UPLC also confirmed that a majority of the population in 1:4 mAv had 4 PEGs conjugated to Avidin (peak 'b' at 4.38 min) followed by a secondary population of mAv with 2 PEGs (peak 'c' at 5.33 min, FIG. 2C). No peak for native Avidin (6.29 min) was found in 1:4 mAv confirming that Avidin was successfully PEGylated. UPLC of 1:2 mAv also confirmed that the majority of Avidin conjugated with two PEGs (FIG. K1, peak 'c' at 5.35 min) followed by configurations containing three PEGs (peak 'b') and one PEG (peak 'd'). Due to this heterogeneity, the physical and transport properties determined, represent the collective behavior of different populations in each formulation.

PEGylation did not reduce mAv's zeta potential (Q) suggesting minimum shielding of cationic charge; its net size was within the 10 nm limit (Table 1, below). As such, its intra-cartilage transport diffusivities (estimated using setup in FIG. 3A) were not affected either (Table 1). The hydrodynamic diameter of Avidin and mAv was estimated from their molecular weights using the Stokes-Einstein equation. The net size of mAv was within the 10 nm limit enabling it to penetrate through the full thickness of cartilage similar to unmodified Avidin.

TABLE 1

Zeta potential (ζ), net size (diameter) and intra-cartilage effective diffusivities ($D_{EFF}$) of Avidin, 1:2 mAv and 1:4 mAv. Data shown as Mean ± SD.

| Formulation | Avidin | 1:2 mAv | 1:4 mAv |
|---|---|---|---|
| ζ (mV) | 18.3 ± 0.5 | 20.3 ± 0.3 | 25.3 ± 0.7 |
| Diameter (nm) | ~7.0 | ~7.6 | ~8.1 |
| $D_{EFF}$ ($cm^2$/s) | 8.4 ± 2.0 × $10^{-8}$ | 2.7 ± 0.5 × $10^{-8}$ | 3.5 ± 1.0 × $10^{-8}$ |

Transport Properties of mAv in Cartilage

Non-equilibrium transport properties of mAv in cartilage were estimated from diffusion curves (FIG. 3A) using a setup described previously [1]. Effective diffusivity ($D_{EFF}$) of mAv decreased 2.5-3× compared to unmodified Avidin, implying slower diffusion rates as a result of PEGylation. There was no significant difference in diffusivities of 1:2 and 1:4 mAv (Table 1).

Figures 3A, 3B, 3C, 3D:
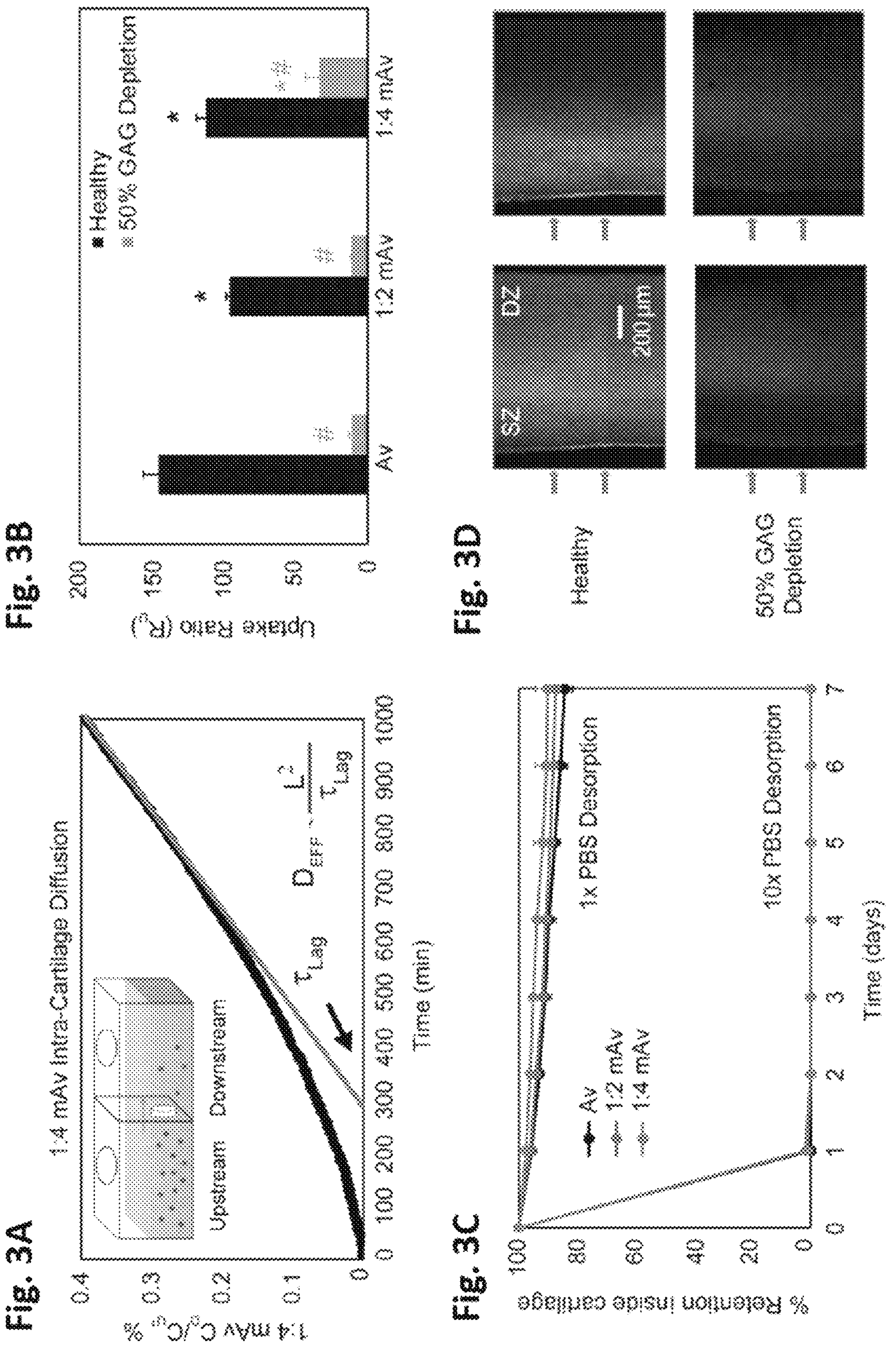
FIG. 3A shows the transport properties of mAv nano-constructs in cartilage. Non-equilibrium diffusion curve of 1:4 mAv in cartilage showing normalized downstream concentration ($C_D$) to upstream concentration (Cu) versus time. $\tau_{Lag}$ was used to estimate effective diffusivity, $D_{EFF}$, in presence of binding interactions within the cartilage. L refers to cartilage thickness.
FIG. 3B shows intra-cartilage cartilage equilibrium uptake of Avidin (Av), 1:2 mAv and 1:4 mAv after 24 h in healthy and 50% GAG depleted arthritic cartilage (* vs respective condition for Av, #vs respective healthy condition, $p<0.05$).
FIG. 3C shows the % retention of Av, 1:2 and 1:4 mAv inside healthy cartilage following desorption in 1×PBS and 10×PBS over 7 days.
FIG. 3D shows confocal microscopy images demonstrating full thickness intra-cartilage penetration of dual labeled 1:4 mAv from superficial zone (SZ) to deep zone (DZ) of healthy and 50% GAG depleted cartilage. Red channel shows Texas Red labeled Avidin and green channel shows presence of FITC labeled PEGs in mAv.

Equilibrium intra-cartilage uptake (Ru) of 1:2 mAv and 1:4 mAv was 1.5× and 1.3× lower compared to Avidin in healthy cartilage, respectively (FIG. 3B), however, mAv still maintained high uptake in cartilage (mean Ru of 96 and 112 for 1:2 mAv and 1:4 mAv, respectively). Furthermore, following 50% GAG depletion to simulate a mid-stage OA condition, as expected, uptake of Avidin, 1:2 mAv and 1:4 mAv dropped by 13.2×, 8.5× and 4.8×, respectively, compared to healthy condition due to the loss of negatively charged GAG binding sites (FIG. 3B). It should, however, be noted that these uptake values are still very high. For example, a mean Ru of 33 for 1:4 mAv implies 33× higher concentration inside cartilage than in the surrounding equilibration bath. 1:4 mAv carriers can, therefore, also be used for targeting early to mid-stage OA cartilage. Additionally, a majority of mAv was retained inside healthy cartilage over at least a 7-day period similar to unmodified Avidin when desorbed in 1× PBS. Desorption in saline bath with high salt concentration (10×PBS) resulted in complete desorption for all species within 24 h highlighting the dominant role of charge interactions (FIG. 3C).

1:4 mAv penetrated through the full thickness of cartilage within 24 h (FIG. 3D), similar to Avidin in both healthy and OA cartilage explants. The green channel shows presence of PEG-FITC while the red channel shows Avidin-Texas Red distribution in cartilage.

Synthesis and Characterization of PEG-Dex-SA, PEG-Dex-GA, PEG-Dex-PA

Figure 4A:
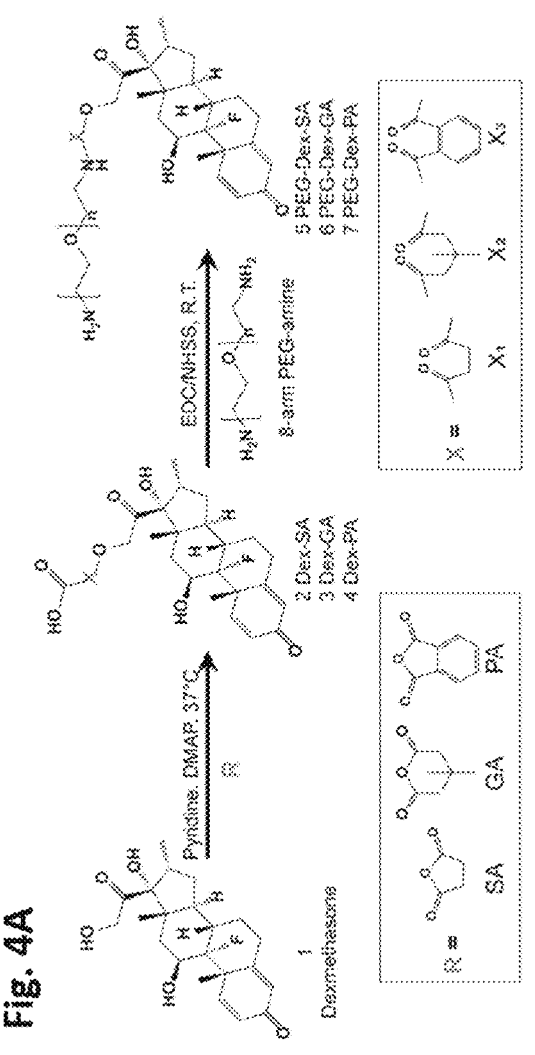
FIGS. 4A-4D show a reaction scheme, release profile and cytotoxicity of PEG-Dex compounds.

Incorporation of carboxyl group in compounds 2, 3 and 4 (FIG. 4A) was verified with the appearance of a yellow spot (stained by bromocresol green) on TLC plate and their yields were estimated as ~92%, ~72% and ~94%, respectively, using HPLC quantitative analysis. PEG-Dex-SA (5), PEG-Dex-GA (6) and PEG-Dex-PA (7) were synthesized by coupling compounds 2, 3 or 4 with 8-arm PEG-amine through EDC/NHS reaction (FIG. 4A). The chemical structure of compounds 1-7 were confirmed by $^1$H-NMR as shown in FIG. 13A-F.

The amount of Dex conjugated to PEG was determined by analytical reverse-phase HPLC. As shown in Table 2, below, compounds 5, 6 and 7 had 6.6±0.5, 1.6±0.4, 3.3±0.5 molecules of Dex on one molecule 8-arm PEG, respectively. After conjugating to Avidin in 1:4 mAv configuration, the DLC for mAv-Dex-SA, mAv-Dex-GA, and mAv-Dex-PA were calculated as 15.7±1.0%, 3.8±0.9%, and 7.8±0.1%, respectively.

TABLE 2

Hydrolysis half-lives of ester linkers between 8-arm PEG and carboxylated derivatives of Dex. Molar ratio of Dex conjugated with PEG for each configuration and the corresponding drug loading content (DLC). Data shown as Mean ± SD.

| Ester linker | PEG-Dex-SA | PEG-Dex-GA | PEG-Dex-PA | PEG-Dex (2:1:1) |
|---|---|---|---|---|
| Half-life (h) | 6.8 ± 0.2 | 79 ± 1.8 | 86 ± 2.3 | 38.5 ± 1.5 |
| Dex:PEG (molar ratio) | 6.6 ± 0.5:1 | 1.6 ± 0.4:1 | 3.3 ± 0.5:1 | 4.6 ± 0.5:1 |
| DLC (%) | 15.70 ± 1.0 | 3.81 ± 0.9 | 7.85 ± 0.1 | 11.1 ± 0.8 |

Figure 4B:
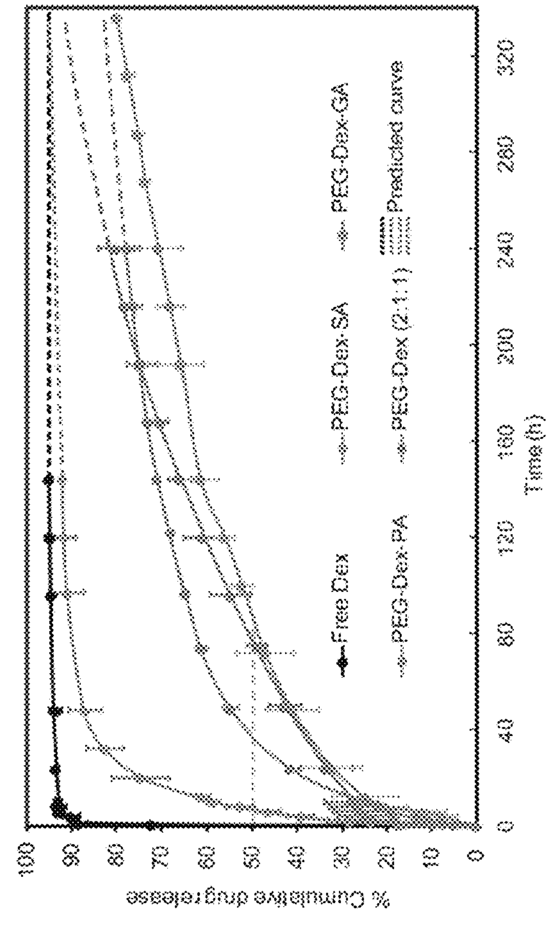
Figure 4C:
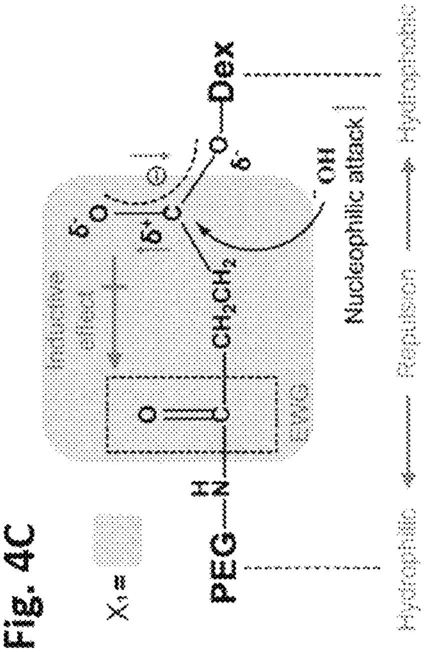

About 70% of Dex was released from PEG-Dex-SA in PBS within the first 24 h resulting in a short release half-life ($t_{1/2}$) of about 6.8 h (FIG. 4B). We addressed this by increasing the carbon spacer length between the ester and adjacent amide by replacing SA with GA or PA to form carboxylic acid derivatives of Dex, which significantly increased the mean release half-lives to 79 h and 86 h for PEG-Dex-GA and PEG-Dex-PA, respectively. These spacers weaken the adjacent carbonyl groups' inductive effect (which reduces the ester's electron density) by donating multiple electrons and stabilizing the ester bond (FIG. 4C). These linkers provide a simple aqueous based way of effectively controlling release rates depending on drugs, disease severity and tissue type. Based on the drug release profiles, compounds 5, 6 and 7 were physically mixed at a 2:1:1 molar ratio by Dex content (PEG-Dex 2:1:1) to develop a controlled release formulation that combined the effects of burst-release from PEG-Dex-SA to reach therapeutic levels within a short period of time and sustained drug release over two weeks from PEG-Dex-GA and PEG-Dex-PA. The resulting Dex release half-life was measured as $t_{1/2}$=38.5±1.5 h. In vivo release half-lives of linkers are expected to be altered due to the presence of proteases, other enzymes and binding with other synovial fluid proteins. Prior work, however, has shown that Dex release via ester hydrolysis did not change in synovial fluid and was similar to that in PBS [4].

Figure 4D:
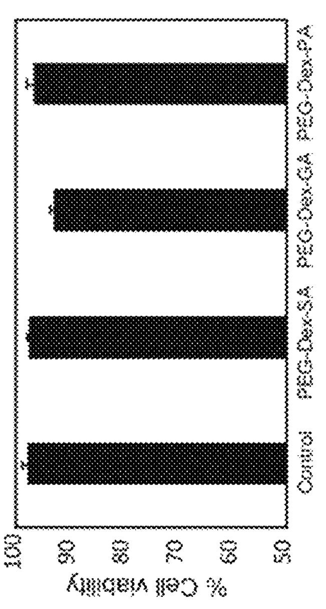

Finally, before conjugating PEG-Dex-SA to Avidin to form fast release mAv-Dex or a combination of PEG-Dex-SA, -GA and -PA in 2:1:1 molar ratio to Avidin to form controlled release mAv-Dex (2:1:1) and testing its bioactivity using cytokine challenged in-vitro cartilage explant culture models, cartilage explants were treated with compounds 5, 6 and 7 (with high equivalent concentration of 100 μM Dex, which is 10× higher than that used in subsequent bioactivity experiments) for 48 h. Treated explants showed similar cell viability as the untreated control condition (FIG. 4D), confirming no cytotoxic effects.

Figure 5A:
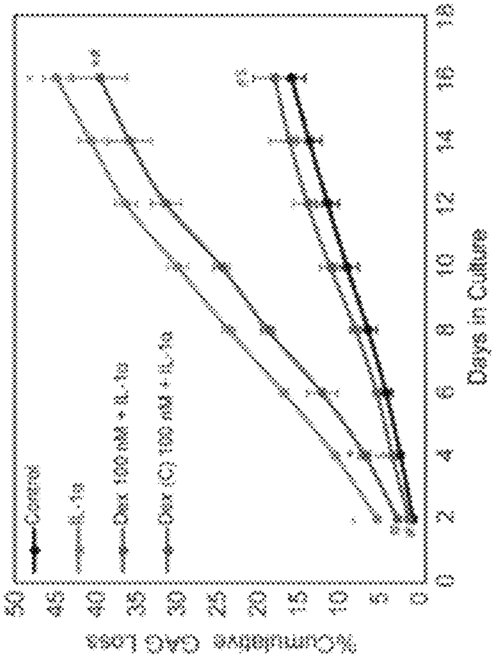
FIG. 5A shows the effectiveness of single dose mAv-Dex treatment in suppressing IL-1α induced GAG loss and chondrocyte death. % cumulative GAG loss over 16 days: IL-1α treated cartilage explants treated a single or continuous (C) dose of 100 nM free Dex.

Bioactivity of Single Dose of mAv-Dex in IL-1α Treated Cartilage Explant Culture OA Model We first compared the effectiveness of single versus continuous (sustained) doses of 100 nM free Dex in suppressing IL-1α induced catabolic activity in cartilage. Treatment with IL-1α significantly increased GAG loss over the 16-day culture period compared to control ($p<0.0001$) (FIG. 5A). A single dose of 100 nM Dex was not effective and a continuous dose of Dex was needed to effectively suppress IL-1α induced GAG loss throughout the culture duration to levels similar to the healthy condition, highlighting the importance of maintaining a sustained drug concentration throughout the culture period.

To evaluate the effect of single dose of mAv-Dex that creates an intra-cartilage drug depot, a concentration of 10 μM Dex was used to provide sustained therapeutic doses of at least 10 nM over the entire culture duration and the biological effects were compared with that of free Dex. The dosing calculations are explained here: Previous work has shown that a sustained (continuous) dosing of 10-100 nM Dex throughout the culture duration is effective in suppressing cytokine induced catabolism [5, 6], which corresponds to a minimum of 0.0001-0.001 nmol inside cartilage, respectively. An initial dose of 10 μM mAv-Dex in the media equilibrates within 24 h resulting in 112× higher concentration inside cartilage than the outside media bath owing to charge interactions (FIG. 3B). Therefore, based on mass balance between the explant and surrounding media, the equilibrium Dex concentration in media is estimated as 2.1 μM, implying an intra-cartilage concentration of ~236 μM (112×2.1 μM), which is equivalent to 2.36 nmol of Dex inside the cartilage disk of 10 μL volume before the first media change at 48 h. Dex release half-life from mAv-Dex in 2:1:1 formulation is 38.5 h (by fitting a single-phase exponential decay model), which means 10 half-lives over 16-day culture period. Based on this, [(½)^] of the initial administered dose will be present in cartilage after 16 days which equals to 0.0023 nmol (0.1% of 2.36 nmol). Therefore, a one-time dose of 10 μM mAv-Dex was used in our experiments as it can maintain therapeutic Dex dosage of at least 10 nM over 2 weeks to suppress cartilage degradation.

Figure 5B:
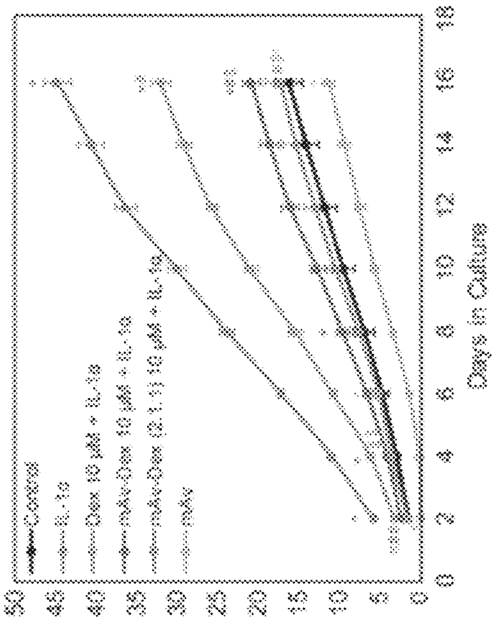
FIG. 5B shows the effectiveness of single dose mAv-Dex treatment in suppressing IL-1α induced GAG loss and chondrocyte death. % cumulative GAG loss over 16 days: IL-1α treated cartilage explants treated single doses of 10 μM free Dex, mAv-Dex or mAv-Dex (2:1:1). A concentration of 10 μM mAv alone in absence of IL-1a was also tested and compared with the control condition (* vs control, #vs IL-1α, $ vs single dose Dex condition, ∧ vs mAv-Dex, $p<0.05$. Statistical markers are color coordinated with the curves. All data enclosed within statistical markers are significant.)

As shown in FIG. 5B, a single dose of 10 μM Dex significantly suppressed IL-1α induced GAG loss throughout the duration of culture ($p<0.0001$ compared to IL-1α condition) but remained significantly elevated compared to the control condition ($p<0.0014$ starting at Day 4), highlighting its short-term therapeutic benefit. Both fast and controlled release mAv-Dex suppressed IL-1α induced GAG loss throughout the culture duration significantly greater than single Dex dose (from Day 4; $p<0.0037$), bringing levels down to that of the untreated control. Controlled release mAv-Dex (2:1:1) had a longer lasting therapeutic response (throughout the culture duration) than the fast release mAv-Dex whose GAG loss levels became statistically different from control condition by Day 8 ($p<0.04$). mAv carrier in 10× higher concentrations than used in mAv-Dex (2:1:1) was associated with no GAG loss. In fact, GAG loss levels measured were lower than that for the control condition, a phenomenon that warrants more probing. We confirmed that the presence of positively charged Avidin did not hinder the activity of cationic DMMB assay as the total GAG measured (i.e. GAG lost to media over the entire culture duration+residual GAG in the cartilage explant) was similar in the untreated control and mAv treated conditions i.e. we were effectively able to measure the total GAG content using the DMMB assay.

Figure 5C:
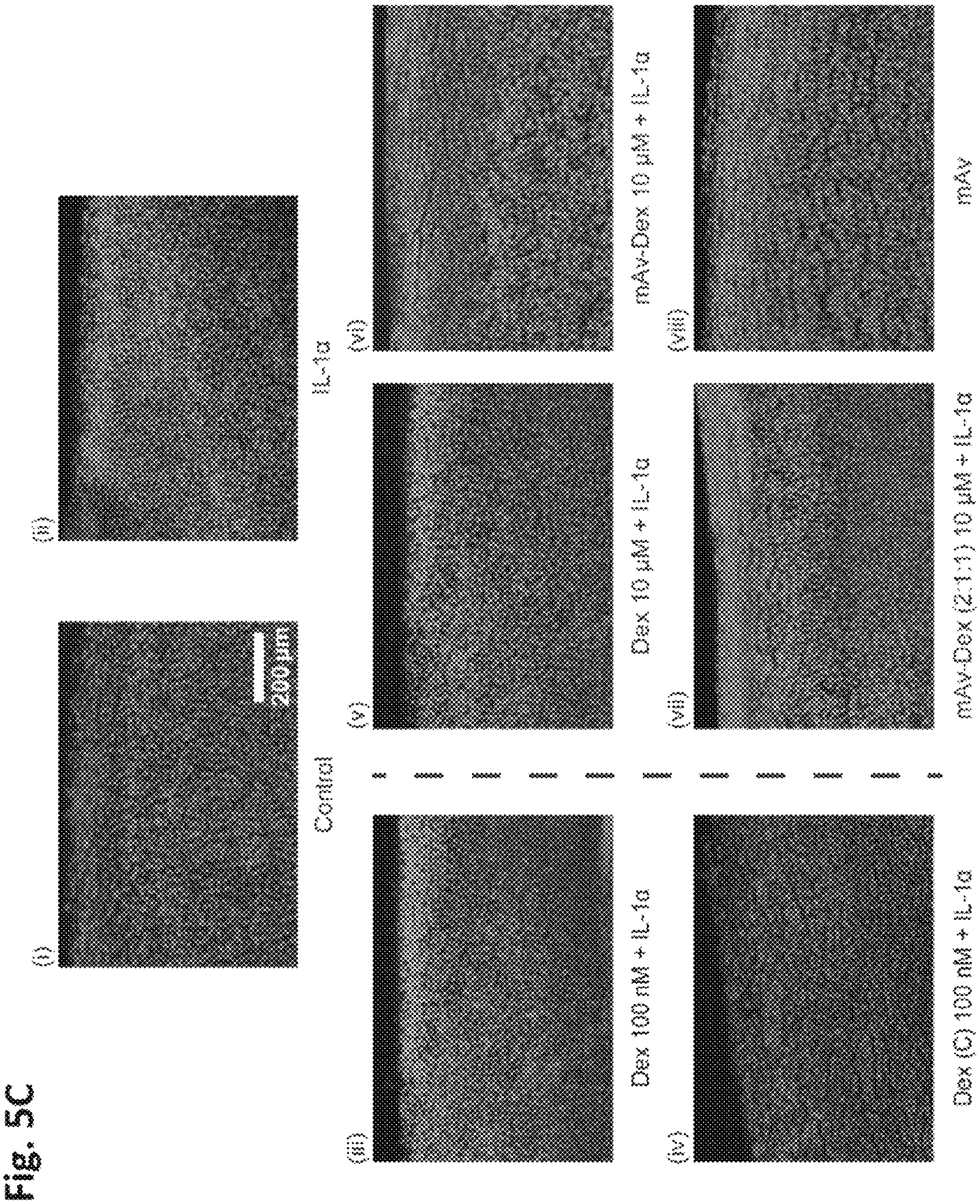
FIG. 5C shows chondrocyte viability after 16 days of culture. Green indicates viable cells and red indicates non-viable cells. Scale bar=200 μm.

Similar trends were observed in Day 16 chondrocyte viability images (FIG. 5C); treatment with IL-1α enhanced cell death which was rescued effectively by the continuous dose but not with a single dose of 100 nM Dex. On the other hand, single dose of both fast and controlled release 10 μM mAv-Dex rescued cell viability similar to continuous dosing condition while a single dose of 10 μM free Dex was not as effective. mAv treatment did not cause any cell death. Some cell death shown in the superficial zone was observed in control explants, along with the location of harvesting from the joint. Additionally, excision of tissues from the joint using punches can also lead to cell death at the cut surfaces.

Figure 6A:
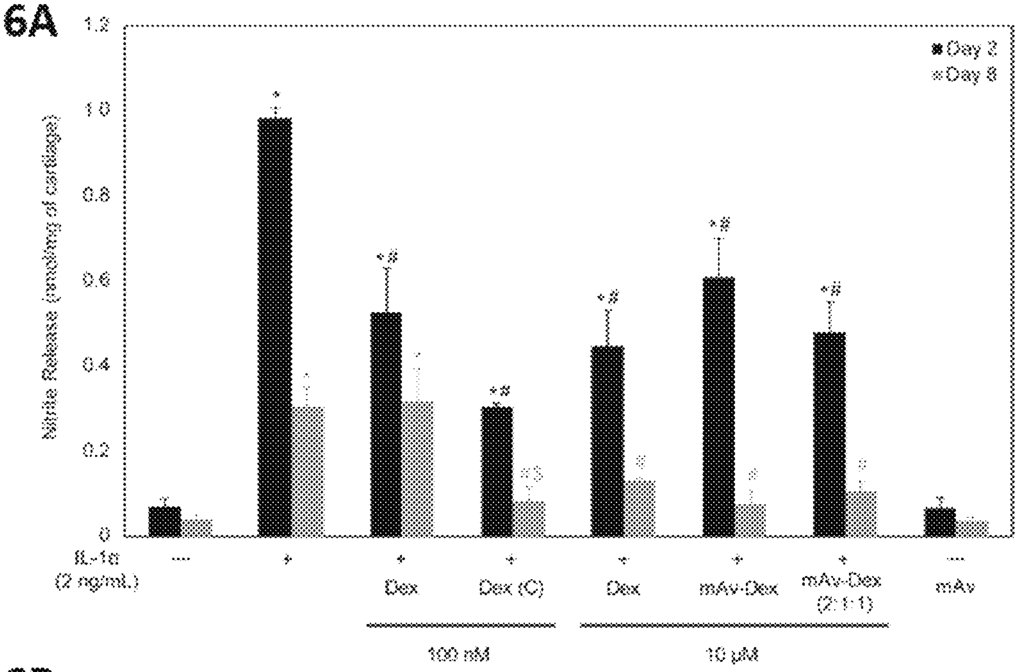
FIG. 6A depicts the effect of mAv-Dex on nitrite release in IL-1α treated cartilage.

Nitrites are a reactive oxygen species (ROS) triggered by an upregulation in inflammatory activity such as the presence of IL-1α in an OA environment. As expected, IL-1α treated explants produced 14.4× and 7.7× higher amounts of nitrite compared to control at 2 and 8 days of culture ($p<0.0001$), respectively (FIG. 6A). Treatment with all Dex containing conditions significantly lowered nitrite synthesis at Day 2 ($p<0.047$ vs IL-1). By Day 8, continuous Dex dose resulted in 3.5× lower nitrite levels compared to single dose of 100 nM Dex. A single dose of mAv-Dex (both controlled and fast release formulations) suppressed nitrite synthesis levels by 1.5-2× compared to a single dose of 10 μM free Dex, bringing levels close to control levels at Day 8. Lastly, there was no difference between mAv and untreated control conditions confirming no associated toxicity/inflammatory effects of mAv. IL-1α reduced cell metabolism rates, however, were not rescued by either Dex or mAv-Dex (FIG. 6B) suggesting the need to incorporate a pro-anabolic drug for a comprehensive and a more effective OA treatment. mAv treatment did not suppress cell metabolism levels.

Figure 7:
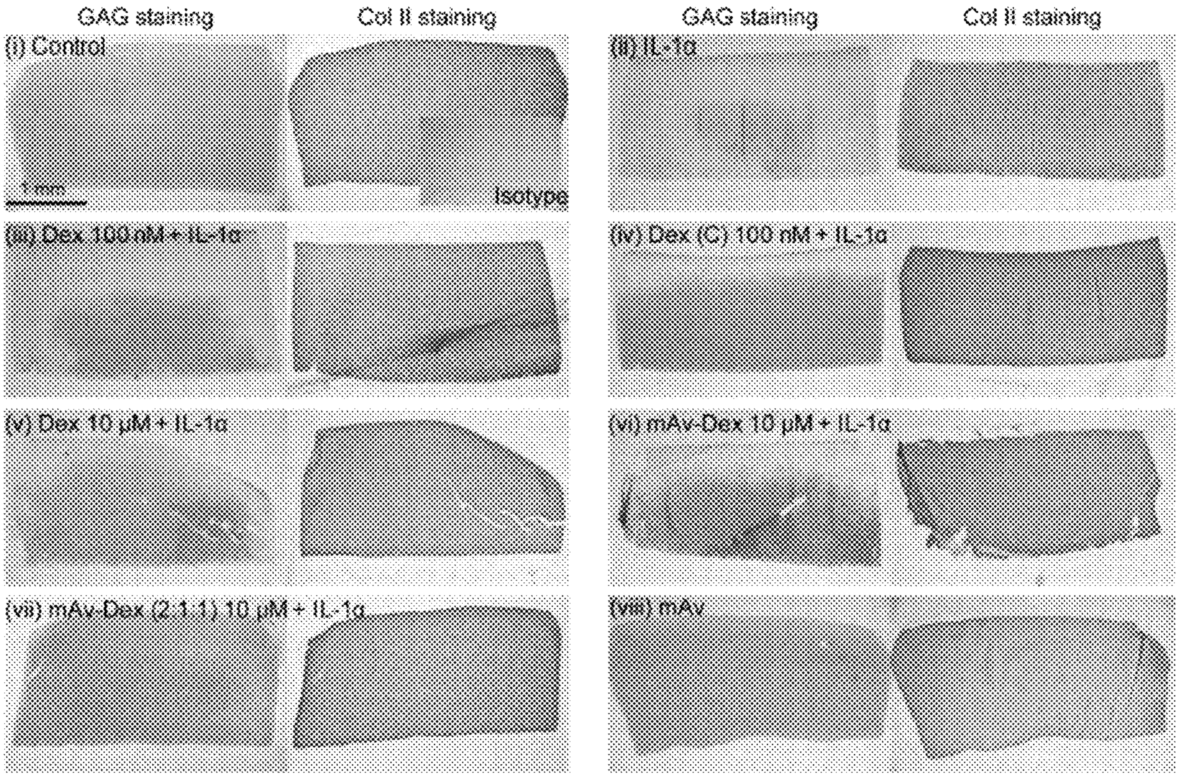
FIG. 7 shows histological and immunohistochemical analysis of cartilage. Cartilage explants stained with Safranin-O and Fast Green (for GAG) or immunostained for collagen type II after a 16-day culture period.

Finally, GAG and collagen content through the explant tissue depth was assessed by histology and immunohistochemistry (FIG. 7). IL-1α treated explants showed visibly low levels of Safranin-O staining compared to controls, indicating significant GAG loss. This IL-1-stimulated GAG loss was mostly rescued by a continuous 100 nM Dex dose, particularly below the superficial layer where chondrocyte viability was maintained (FIG. 5A-C); however, staining was marginally affected by a single 100 nM dose. At 10 μM, a single dose free Dex protected GAG content to a greater extent than at 100 nM. The fast release formulation of 10 μM mAv-Dex did not clearly alter GAG staining over 10 μM free Dex. This may be partly explained by the limited linear range of GAG staining by Safranin-O, which can mask more subtle differences in total GAG levels; in this regard, Safranin-O staining can better reflect the localization of GAG loss. In contrast to the fast release formulation, the controlled release mAv-Dex formulation displayed GAG staining that more closely approximated control disks compared to the other IL-1-challenged groups. Furthermore, mAv alone did not have any detrimental effects on tissue Safranin-O staining. Total type II collagen levels were not visibly affected by IL-1α treatment over the 16 days test period (FIG. 7).

DISCUSSION

Here we designed a cartilage penetrating and binding mAv nano-construct that can be conjugated with a variety of small molecule drugs or their combinations using hydrolysable ester linkers with tunable drug release rates. The nano-construct incorporates four 8-arm PEGs, providing 28 sites for drug conjugation per mAv compared to only 4 sites in previous designs [4]. As a result, to deliver a one-time dose of 10 μM Dex to cartilage explants, less than 1 μM Avidin was needed which is within safe limits. Previous research has shown that an Avidin concentration less than 100 μM does not cause any GAG loss or affect chondrocyte viability or biosynthesis rates of proteins and GAGs in bovine cartilage explants. mAv was designed to keep its net size within the previously determined 10 nm size limit for unhindered diffusion into native cartilage and its net charge was shown to be not shielded by addition of multi-arm PEGs (Table 1). As a result, mAv exhibited similar intra-cartilage transport properties as native Avidin; it penetrated through the full thickness of cartilage within 24 h, resulting in a high intra-cartilage uptake (mean Ru of 112 for 1:4 mAv) and long-term retention as the majority of it remained bound within the cartilage over a 7-day desorption period (the duration of experiment conducted) in 1×PBS (FIG. 3A-D). mAv also showed high uptake (mean Ru of 33) in 50% GAG depleted cartilage explants, implying that it can be used for delivering drugs to mid- to late-stage arthritic cartilage. While some binding of mAv with negatively charged groups of synovial fluid can be expected, our previous work has confirmed that the high negative FCD of cartilage enables rapid diffusion of IA injected native Avidin into rat and rabbit cartilage [2,3] resulting in high uptake and long-term retention despite the presence of synovial fluid and dynamic compression-induced convective flow in animal knee joints. Since mAv's net size and charge properties are similar to that of native Avidin, similar intra-joint kinetics are expected.

First, we conjugated Dex as an example OA drug with 8-arm PEG using hydrolysable ester linkers derived from SA (FIG. 4A). However, the fast-release ester linker in PEG-Dex-SA had a half-life of 6.8±0.2 h, which burst-released a majority of Dex prior to the first media change at 48 h of culture (FIG. 4B). When conjugated with Avidin (fast release mAv-Dex), this resulted in significantly improved therapeutic benefit compared to free Dex throughout 16 days of culture. However, compared to continuous dose of 100 nM Dex, the fast release mAv-Dex resulted in higher GAG loss starting at Day 8 (FIG. 5B). Thus, in order to maintain therapeutic doses of Dex throughout the culture duration, we used GA or PA to synthesize carboxylated derivatives of Dex that increased the half-life of the ester linkers in PEG-Dex-GA and PEG-Dex-PA to 79±1.8 h and 86±2.3 h, respectively. The hydrolysis of an ester bond begins when hydroxide ions of water attack the electrophilic carbon in the ester bond, breaking the p-π conjugation of ester bond creating a tetrahedral intermediate. Since the adjacent carbonyl group from the amide bond tends to compete with and withdraw electrons from the ester bond (inductive effect) resulting in a decrease in the ester bond's electron density, the carbon in ester bond becomes more electrophilic and reactive to nucleophilic attack from hydroxide ion causing a faster release rate (as in the case of compound 5, PEG-DEX-SA in FIG. 4C). Furthermore, hydrophobic Dex conjugated to hydrophilic polymer PEG can produce repulsive forces, thereby accelerating the separation of Dex from PEG. As for compound 6, the GA cross-linker will increase the carbon length between the ester and amide bonds thus weakening the inductive effect of the carbonyl group. The two methyl groups in the GA branched chain can also donate electrons, thereby stabilizing the ester bond. Similarly, the phenyl group in PA can donate numerous electrons to the ester bond (compound 7). Our previous research has shown that a combination of fast and slow releasing linkers can yield a more effective treatment over a long period of time than a complex containing only one of the linkers [4]. Thus, we used ester linkers derived from SA, GA and PA in a molar ratio of 2:1:1 to formulate a controlled release mAv-Dex that enabled 50% release of Dex in 38.5 h followed by a sustained release of the remaining drug over the next two weeks.

As a result, single 10 μM dose of controlled release mAv-Dex (2:1:1) completely suppressed IL-1α induced GAG loss bringing levels down to that of untreated control throughout the 16-day culture period (FIGS. 5B and 7), mimicking the continuous 100 nM Dex condition (FIGS. 5A and 7). Its therapeutic effect was significantly better than that of the fast release mAv-Dex where ester linker was derived from SA only and had a short half-life of 6.8 h. Similar trends were observed in Day 16 chondrocyte viability images (FIG. 5C) where single dose of both fast and controlled release 10 μM mAv-Dex rescued cell viability similar to continuous 100 nM free Dex while a single dose of 10 μM free Dex was not effective. Treatment with mAv alone did not have any detrimental biological effect even at 10× higher concentrations than used in mAv-Dex (2:1:1).

We chose Dex as an example drug as it is a broad spectrum glucocorticoid (GC) with anti-catabolic properties and has intra-cellular receptors inside cartilage and in synovium and can elicit disease modifying effects as well as suppress OA induced pain and inflammation. Effectiveness of GCs, however, has been a subject of controversy showing both chondroprotective and deleterious effects following IA injection. Their effectiveness depends largely on frequency, dosage and the duration of treatment. GCs like Dex, triamcinolone acetonide (TCA) and prednisone are used in high doses and multiple times (up to 100 mM compared to one time 10 μM dose used in the present study) for OA pain relief due to their short intra-joint residence time causing bone resorption, cell apoptosis and systemic toxicity. For example, a recent human clinical trial (NCT01230424) concluded that IA injections of 40 mg TCA every 3 months for 2 years in patients with symptomatic knee OA resulted in greater cartilage loss compared to saline, emphasizing the critical need for targeted, low dose sustained therapy. A recent study also showed that multiple intra-articular injections of Dex (2.5 mg every 3 days or 0.5 mg/kg) were needed to significantly reduce inflammation and protect cartilage in a bone drill rabbit model of PTOA; this high multi-dose regimen, however, resulted in systemic toxicity in vital organs [7]. Nevertheless, a recent clinical trial (NCT01692756) concluded that early intervention using two doses of 40 mg TCA within 10 days of ACL rupture was able to prevent injury induced early chondral changes. While more follow up studies are needed to conclude meaningful clinical difference in overall outcome, there remains continued interest in using GCs as disease modifying agents for OA/PTOA treatment and not just for symptomatic relief. It is, however, imperative to develop strategies in parallel that can target cartilage and deliver therapeutic low drug doses over several days to weeks to avoid toxicity associated with multiple injections of high drug doses.

Recent research has focused on developing IA drug delivery systems, including drug-encapsulating microparticles, polymeric micelles, liposomes, aggregating hydrogels and peptides. The majority of carrier systems cannot penetrate the dense, negatively charged cartilage; consequently, while some have shown promise for suppressing pain and inflammation originating from the synovium and surrounding joint capsule, they are not effective at stimulating disease-modifying responses in chondrocytes. For example, recently intra-joint sustained release formulations of TCA encapsulated within micron sized PLGA particles (Flexion Therapeutics, Burlington, VT, USA) were approved by the FDA for OA pain and inflammation, but such systems naturally use high drug doses to induce biological response (40-60 mg of drug). Flexion's microsphere based TCA delivery (FX006, 32 mg drug dose administered) showed prolonged synovial fluid joint residency (until Week 12), diminished peak plasma levels and thus reduced systemic exposure compared to free TCA following a single IA injection in patients with knee OA in a Phase II open label study. Their Phase III, multicenter, double-blinded, 24-week study concluded that a single IA injection of FX006 provided significant improvement in average-daily-pain (ADP)-intensity scores compared to saline (placebo) but no significant improvements in OA pain were observed when compared to the free drug. In a Phase III post-hoc study, where efficacy of FX006 was evaluated in a subgroup of participants with unilateral knee OA only (as bilateral knee pain has emerged as a cofounding factor in clinical trials evaluating the effect of single IA injection), significant improvement in WOMAC or ADP scores were reported for FX006 compared with both saline and free drug over a period of 5-6 months. While these are promising data for longer lasting pain relief with a single IA injection, delivery systems like mAv can target cells inside cartilage to elicit long-term disease modifying effect to restore joint function. Joint inflammation has a complex etiology that involves not only the synovium but also subchondral bone and articular cartilage. Therefore, effective treatments will likely need to deliver OA drugs into cartilage as well as to surrounding tissues. We predict that gradual release of drug from intra-cartilage drug depot enabled by mAv delivery can significantly inhibit IL-1α signaling, for example, in both cartilage and nearby synovium and other tissues inside the joint, and thus can provide long-term pain and inflammation relief along with restoring joint function. Future studies will investigate this.

Figure 6B:
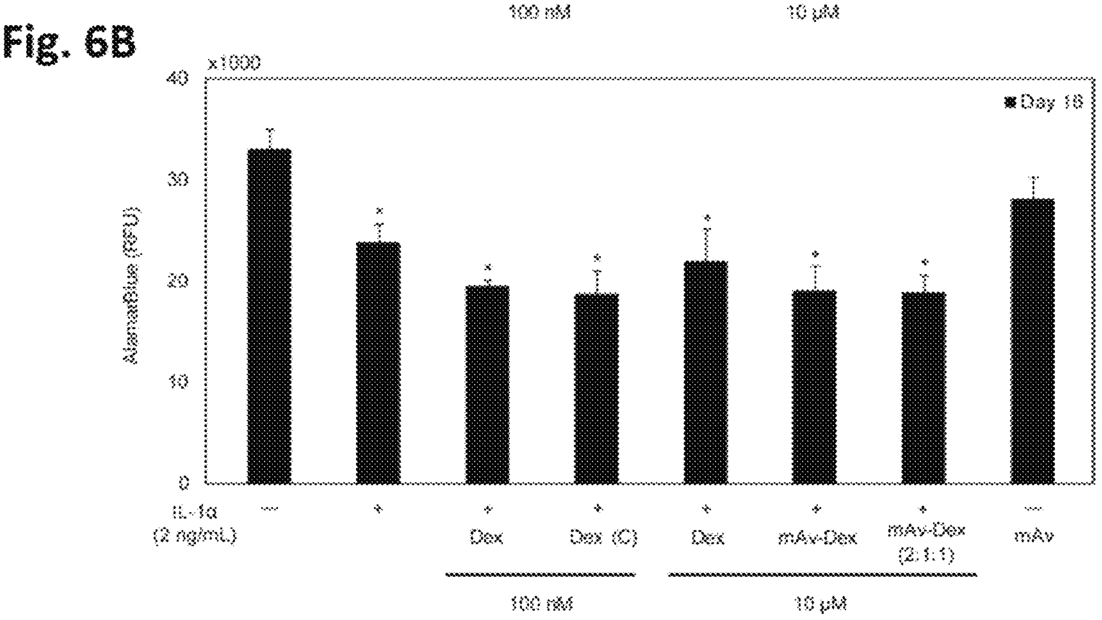
FIG. 6B depicts the effect of mAv-Dex on cell metabolism in IL-1α treated cartilage.

While a single dose of mAv-Dex effectively suppressed cytokine-induced catabolic activity, it was unable to rescue anabolic activity within cartilage explants (FIG. 6B). Dex is known as a potential OA prophylactic agent that inhibits production of matrix metalloproteinases (MMPs), NO and inflammatory cytokines in OA joints. When combined with a pro-anabolic factor like insulin-like growth factor 1 (IGF-1), it can effectively also reverse cytokine-induced inhibition of GAG synthesis. Thus, a combination drug therapy comprising of an anti-catabolic agent like Dex that can induce broad spectrum inhibition of cytokine-related degradation, maintain cell viability along with a pro-anabolic factor like IGF-1 or Kartogenin that can stimulate biosynthesis of viable chondrocytes and replenish cartilage matrix components like aggrecans and collagens is a better approach than monotherapy with one drug. Multiple drugs can be conjugated using similar chemistry to mAv and their release rates can be modulated by varying the ratio of ester linkers derived from SA, GA and PA or designing new types of linkers based on the mechanism explained earlier.

Thus, by using charge interactions, our mAv nano-construct offers multiple advantages of (i) converting cartilage from a barrier to drug entry into a reservoir of drugs that can prevent rapid exit from synovial joint, (ii) accumulating higher drug dose at the cell and matrix target sites and (iii) presenting multiple sites for covalent conjugation of more than one drug for combination therapy. In summary, a charge-based cartilage homing drug delivery platform like this can, potentially, elicit disease modifying effects as well as facilitate long-term symptomatic pain and inflammation relief by enhancing tissue specificity and prolonging intra-cartilage residence time of OA drugs.

The mechanism of mAv targeting of cartilage and drug delivery is summarized as follows (FIG. 1): Following its intra-articular administration, mAv-Dex can rapidly penetrate through the full thickness of negatively charged cartilage in high concentrations due to electrostatic interactions thereby creating an intra-cartilage drug depot. The optimal net positive charge of mAv enables its rapid and high intra-cartilage uptake (112×) and long-term retention via weak-reversible binding with negatively charged aggrecans. Therapeutic doses of drug (Dex) is then released via hydrolysis from controlled release mAv-Dex (2:1:1) over 2 weeks, which can diffuse into chondrocytes to bind with its glucocorticoid receptors triggering downstream signaling pathways and suppressing OA associated catabolic activity. This intra-cartilage depot drug delivery platform can be used to deliver a variety of drugs or combination of drugs and enable OA treatment with only a single injection of low drug doses thereby eliminating toxicity issues associated with multiple injections of high drug doses that are currently needed to maintain sustained drug doses within the joint.

Chemical Synthesis of CPC-IGF-1

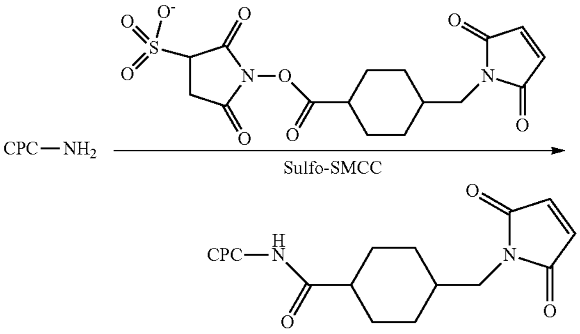

(CPC-maleimide)

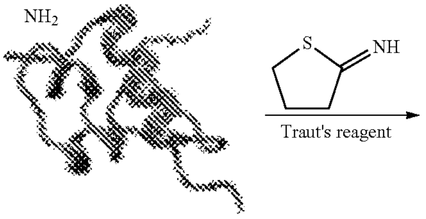

(IGF-1)

-continued

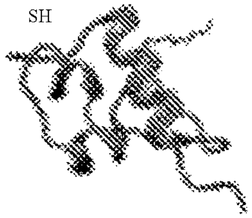

(Thiolated IGF-1)

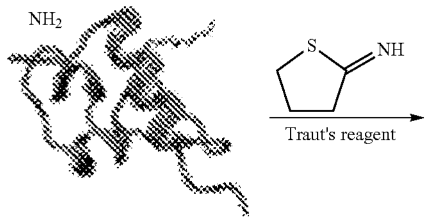

(IGF-1)

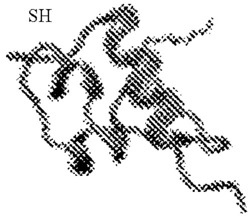

(Thiolated IGF-1)

Due to the highest intra-cartilage uptake, high intra-cartilage retention and full-thickness penetration, CPC+14 sequence was chosen as an exemplary candidate for drug delivery to cartilage. CPC+14 was conjugated to IGF-1 using maleimide chemistry. Briefly, the fluorescently labeled CPC+14 was modified with a lysine group at the C-terminus (CPC+14-K). CPC+14-K was then modified with a maleimide group through reaction with amine-reactive N-hydroxysuccinimide (NHS ester) bifunctional maleimide linker, Sulfosuccinimidyl-4-(N-maleimidomethyl)cyclohexane-1-carboxylate (Sulfo-SMCC) (see scheme above). Since all the cysteines in IGF-1 structure actively form disulfide bridges which makes them not available for reaction with maleimide groups, reactive sulfhydryl (SH) groups were added to lysine residues on IGF-1. For this aim, SH groups were introduced to IGF-1 amine groups through reaction with Traut's reagent to obtain IGF-1-SH. CPC-IGF-1 was subsequently achieved through mixing of IGF-1-SH with CPC-Maleimide.

Chemical Synthesis of CPC-IOX

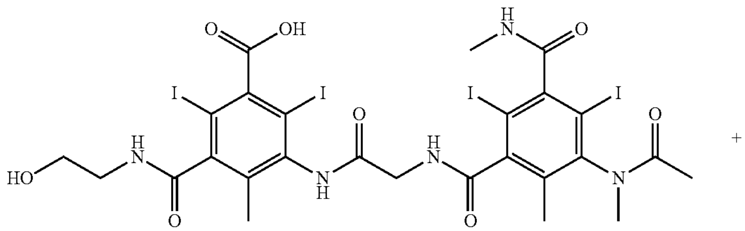

IOX

-continued

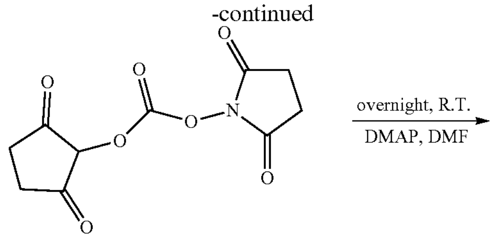

N,N'-Disuccinimidyl carbonate (DSC)

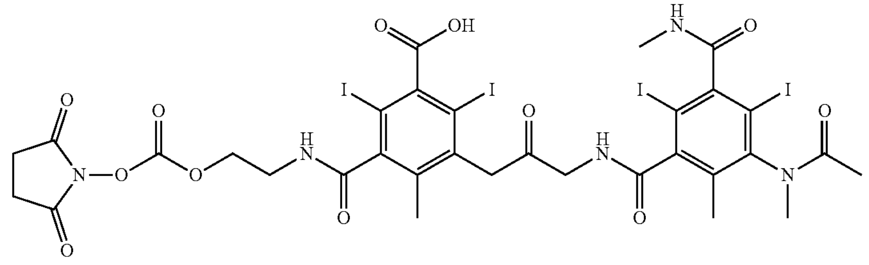

IOX-succinimidyl carbonate (IOX-SC)

CPC (+8) was conjugated to IOX through reaction of arginine guanidinium group with an amine reactive succinimidyl carbonate moiety introduced at hydroxyl functional group of IOX. For this purpose, following (FIG. 6), 58.1 mg of IOX was dissolved in 1 mL of DMF (46.0 μmol, 1 equiv.). 58.8 mg of N,N'-Disuccinimidyl carbonate (DSC) (229.0 μmol, 5 equiv.) and 32.5 mg of 4-Dimethylaminopyridine (DMAP) (229.0 μmol, 5 equiv.) were also dissolved in 0.5 mL of DMF. Solutions of DSC and DMAP were slowly added to IOX solution and reacted overnight at room temperature under stirring. The IOX-succinimidyl carbonate (IOX-SC) conjugate was precipitated using diethyl ether and collected for lyophilization through centrifugation. “(RRAAA)3RR” disclosed as SEQ ID NO: 5.

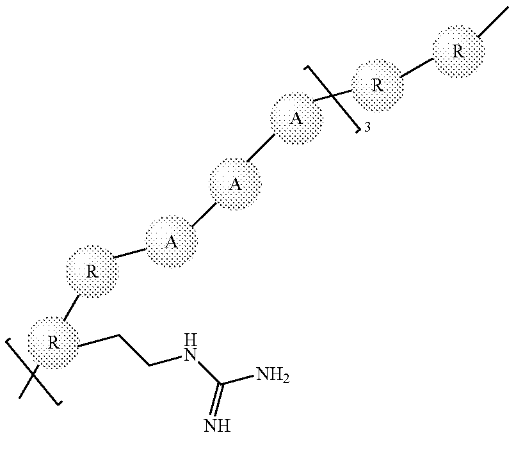

CPC (+8)

+

-continued

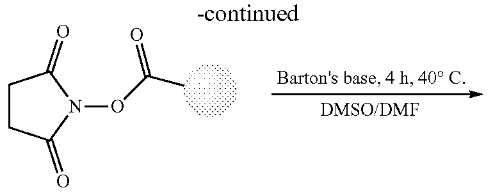

IOX-SC

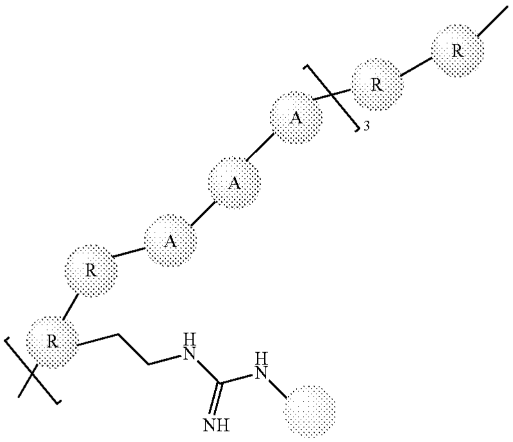

CPC-IOX

There were no primary amines available in the CPC+8 to react with IOX-SC group since the N-terminus of the peptide was modified with 5-FAM. Therefore, the guanidinium groups of CPC+8 were deprotonated using Barton’s base to facilitate their reaction with the amine reactive succinimidyl carbonate introduced on IOX following, similar to reaction between active esters and guanidine groups of arginine. For this aim, 0.05 mg of CPC+8 was dissolved in 0.05 ml of DMSO (20.2 μmol, 1 equiv.) and 0.15 mg of IOX-SC (106.5 μmol, 5.3 equiv.) was dissolved in 0.05 ml of DMF. The solutions were mixed and reacted at 40° C. for 4 h under constant shaking by addition of 1 μl of Barton’s base. The final product was lyophilized and stored.

Cartilage Uptake of CPC-IOX

Figure 14A:
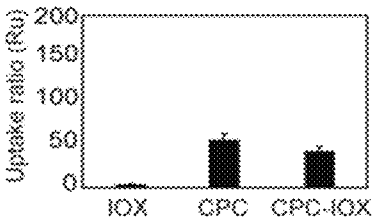
FIG. 14A relates to uptake of CPC-IOX and shows the equilibrium uptake ratio of CPC-IOX in cartilage.
Figure 14B:
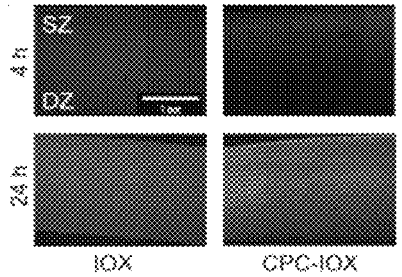
FIG. 14B relates to uptake of CPC-IOX and contains confocal images showing depth of penetration of CPC-IOX in cartilage.
Figure 14C:
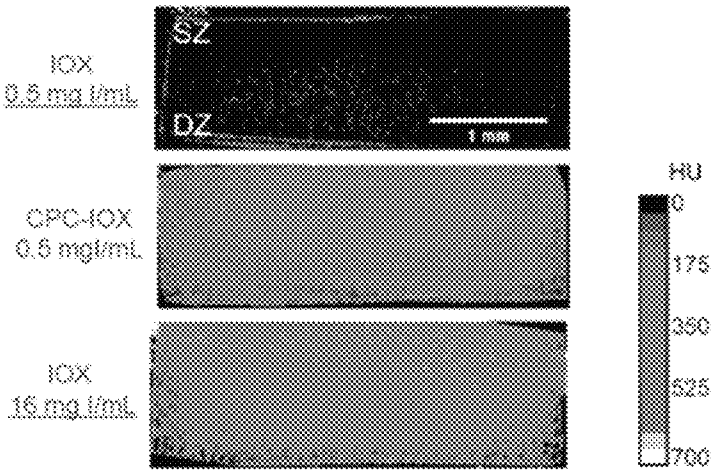
FIG. 14C relates to uptake of CPC-IOX and is a 2D color map of CT attenuation using CPC-IOX.

CPC+8-IOX demonstrated 63 times higher uptake ratio compared to pristine IOX (FIG. 14A). Additionally, CPC+8-IOX penetrated through the full thickness of cartilage within 24 h (FIG. 14B). The 2D color maps demonstrated that a low 0.5 mgI/mL of CPC+8-IOX produced high attenuation and spatial distribution similar to 16 mgI/mL IOX. However, same concentration of IOX (0.5 mgI/mL did not induce any signal) (FIG. 14C). Therefore, upon conjugation with CPC+8, the required concentration of IOX for effective cartilage CT imaging attenuation was reduced by 32 times owing to the electrostatic interactions between the CPC+8 modified IOX with the negatively charged cartilage GAGs. Additionally, attenuation of IOX was mostly at the superficial zone of cartilage while CPC+8-IOX attenuation was the highest at the deep zone of cartilage, which correlates directly with the higher density of negatively charged GAG groups in the deep zone of cartilage.

Cartilage CT Imaging with mAv-IOX

Figure 15:
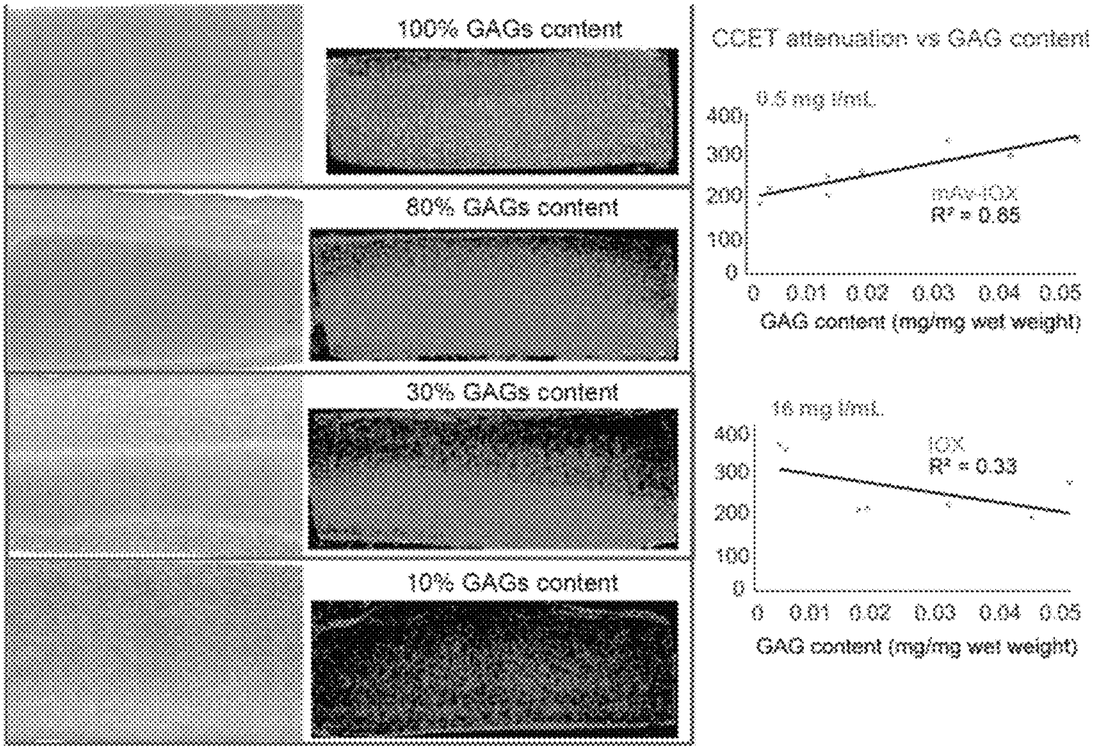
FIG. 15 shows mAv-IOX produces strong CT signal in cartilage explants with varying degree of GAG content (R squared value of 0.85) indicating that the technology can be used for staging arthritis severity, The safranin staining in the first column shows presence of GAG in cartilage explants.

FIG. 15 shows that mAv-IOX is significantly more effective in producing a CT signal in cartilage explants with varying arthritis severity, which was simulated by depleting the negatively charged glycosaminoglycans (GAGs) from the tissue samples using an enzyme. The CT signal correlated strongly with spatial distribution of GAGs inside cartilage. A strong positive correlation was observed between the mean CT attenuation using mAv-IOX, which was not possible with IOX alone.

REFERENCES

1. A. Vedadghavami, et al., Cartilage penetrating cationic peptide carriers for applications in drug delivery to avascular negatively charged tissues, Acta biomaterialia, 93 (2019) 258-269.10.1016/j.actbio.2018.12.004
2. A. G. Bajpayee, et al., A rabbit model demonstrates the influence of cartilage thickness on intra-articular drug delivery and retention within cartilage, J Orthop Res, 33 (2015) 660-667.10.1002/jor.22841
3. A. G. Bajpayee, et al., Sustained intra-cartilage delivery of low dose dexamethasone using a cationic carrier for treatment of post traumatic osteoarthritis, Eur Cell Mater, 34 (2017) 341.10.22203/eCM.v034a21
4. A. G. Bajpayee, et al., Charge based intra-cartilage delivery of single dose dexamethasone using Avidin nano-carriers suppresses cytokine-induced catabolism long term, Osteoarthritis Cartilage, 24 (2016) 71-81.10.1016/j.joca.2015.07.010
5. N. M. Green, A Spectrophotometric Assay for Avidin and Biotin Based on Binding of Dyes by Avidin, Biochem J, 94 (1965) 23C-24C.10.1042/bj0940023c
6. R. W. Farndale, C. A. Sayers, A. J. Barrett, A direct spectrophotometric microassay for sulfated glycosaminoglycans in cartilage cultures, Connect Tissue Res, 9 (1982) 247-248.10.3109/03008208209160269
7. K. D. Huebner, N. G. Shrive, C. B. Frank, Dexamethasone inhibits inflammation and cartilage damage in a new model of post-traumatic osteoarthritis, J Orthop Res, 32 (2014) 566-572.10.1002/jor.22568

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A complex, comprising:

a residue of a contrast agent and a cationic peptide;

wherein the net charge of the cationic peptide is +7 to +20 inclusive;

the residue of the contrast agent is covalently bonded to the cationic peptide;

the contrast agent is selected from the group consisting of diatrizoate, metrizoate, iothalamate, and ioxaglate; and the cationic peptide is selected from the group consisting of: RRAAAARRAAAARRAAAARR (SEQ ID NO: 1);

RRRRAARRRAARRRAARRRR (SEQ ID NO: 2);

$(ARRRAARA)_4$ (SEQ ID NO: 3); and

RRRRRRRRRRRRRRRRRRRR (SEQ ID NO: 4).

2. The complex of claim 1, wherein the cationic peptide is (SEQ ID NO: 1)
RRAAAARRAAAARRAAAARR.

3. The complex of claim 1, wherein the contrast agent is ioxaglate.

4. The complex of claim 1, wherein the cationic peptide is (SEQ ID NO: 2)
RRRRAARRRAARRRAARRRR.

5. A complex, comprising:

a residue of a contrast agent and a cationic peptide;

wherein the net charge of the cationic peptide is +7 to +20 inclusive;

the residue of the contrast agent is covalently bonded to the cationic peptide; and the cationic peptide is selected from the group consisting of: RRAAAARRAAAARRAAAARR (SEQ ID NO: 1);

RRRRAARRRAARRRAARRRR (SEQ ID NO: 2);

$(ARRRAARA)_4$ (SEQ ID NO: 3); and

RRRRRRRRRRRRRRRRRRRR (SEQ ID NO: 4).

6. The complex of claim 5, wherein the cationic peptide is RRAAAARRAAAARRAAAARR (SEQ ID NO: 1).

7. The complex of claim 5, wherein the cationic peptide is (SEQ ID NO: 2)
RRRRAARRRAARRRAARRRR.

8. The complex of claim 3, wherein the cationic peptide is RRAAAARRAAAARRAAAARR (SEQ ID NO: 1).

9. The complex of claim 3, wherein the cationic peptide is RRRRAARRRAARRRAARRRR (SEQ ID NO: 2).

10. The complex of claim 1, wherein the cationic peptide is $(ARRRAARA)_4$ (SEQ ID NO: 3).

11. The complex of claim 1, wherein the cationic peptide is RRRRRRRRRRRRRRRRRRRR (SEQ ID NO: 4).

12. The complex of claim 5, wherein the cationic peptide is $(ARRRAARA)_4$ (SEQ ID NO: 3).

13. The complex of claim 5, wherein the cationic peptide is RRRRRRRRRRRRRRRRRRRR (SEQ ID NO: 4).

* * * * *

SEQUENCE LISTING

```
Sequence total quantity: 5
SEQ ID NO: 1            moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 1
RRAAAARRAA AARRAAAARR                                            20

SEQ ID NO: 2            moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 2
RRRRAARRRA ARRRAARRRR                                            20

SEQ ID NO: 3            moltype = AA  length = 32
FEATURE                 Location/Qualifiers
REGION                  1..32
                        note = Description of Artificial Sequence: Synthetic
                         polypeptide
source                  1..32
                        mol_type = protein
```

-continued

```
                         organism = synthetic construct
SEQUENCE: 3
ARRRAARAAR RRAARAARRR AARAARRRAA RA                                   32

SEQ ID NO: 4             moltype = AA  length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 4
RRRRRRRRRR RRRRRRRRRR                                                 20

SEQ ID NO: 5             moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 5
RRAAARRAAA RRAAARR                                                    17
```